United States Patent [19]

Chatterjee et al.

[11] Patent Number: 5,474,935

[45] Date of Patent: Dec. 12, 1995

[54] ADENO-ASSOCIATED VIRUS (AAV)-BASED EUCARYOTIC VECTORS

[75] Inventors: Saswati Chatterjee; K. K. Wong, Jr., both of Sierra Madre, Calif.

[73] Assignee: The United States of America as represented by the Department of Health and Human Services, Washington, D.C.

[21] Appl. No.: 145,306

[22] Filed: Nov. 3, 1993

Related U.S. Application Data

[63] Continuation of Ser. No. 752,899, Aug. 26, 1991, abandoned, which is a continuation of Ser. No. 527,195, May 23, 1990, abandoned.

[51] Int. Cl.⁶ .................... C12N 15/86; C12N 15/35; C12N 5/10; A61K 48/00
[52] U.S. Cl. ............... 435/320.1; 424/93.1; 424/93.2; 435/172.3; 935/22; 935/32; 935/57
[58] Field of Search ................. 435/320.1, 172.3

[56] References Cited

U.S. PATENT DOCUMENTS

| | | | |
|---|---|---|---|
| 4,689,320 | 8/1987 | Kaji | 536/27 X |
| 4,751,180 | 6/1988 | Cousens et al. | 435/69.7 |
| 4,797,368 | 1/1989 | Carter et al. | 435/320.1 |
| 4,889,802 | 12/1989 | Parslow et al. | 435/69.1 |

OTHER PUBLICATIONS

F. L. Moolten (1987) Medical Hypotheses 24:43–51.
E. Gilboa (1988) Adv. Exp. Med. Biol: Mol. Biol. Hemopoiesis 24:29–33.
D. Baltimore (1988) Nature 335:395–396.
E. C. M. Mariman (1985) Nature 318:414.
J. S. Lebkowski et al Mol. Cell. Biol. 8, 3988–3996 (1988).
D. LaFace et al Virology. 162, 483–486 (1988).
J. C. Sanford (1988) J. Theor. Biol. 130:469–480.
F. Wong-Staal (1989) Serono Symposia 59:1–8.
S. Chatterjee et al (1992) Science 258:1485–1488.
M. I. Johnston et al. (1993) Science 260:1286–1293.

Primary Examiner—Jacqueline M. Stone
Assistant Examiner—Johnny F. Railey, II
Attorney, Agent, or Firm—Foley & Lardner

[57] ABSTRACT

The present invention relates to adeno-associated virus (AAV)-based eucaryotic vectors and uses thereof. Such vectors may, for example, be used to down regulate any targeted viral or cellular gene whose sequence is known. Furthermore, the vectors may also be used to cause the expression of proteins.

11 Claims, 22 Drawing Sheets

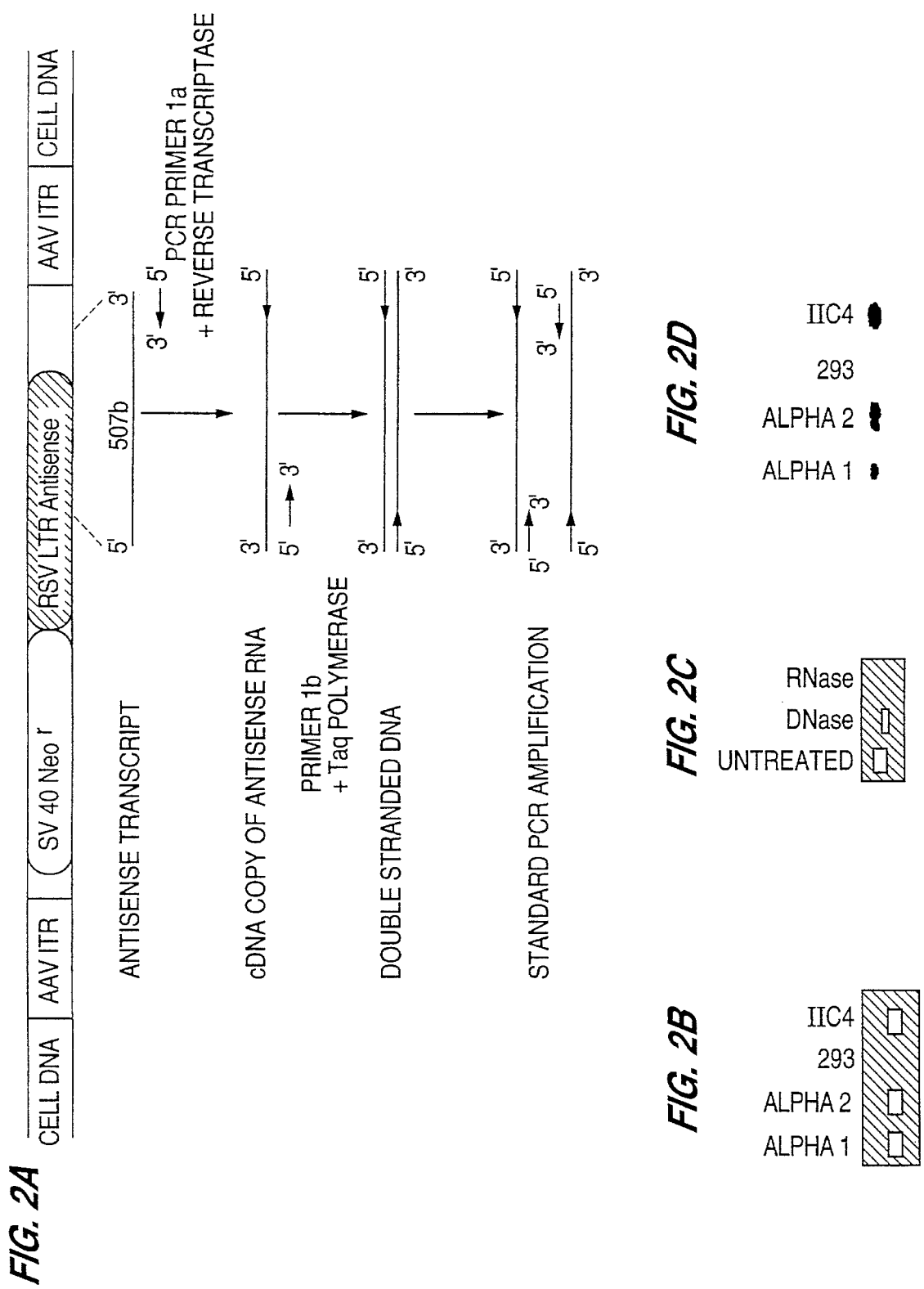

PROBE: pHXB: 3'

IIC4   293

9kb →
4kb →
2kb →

PROBE: ACTIN

IIC4   293

1.7kb →

RIBOSOMAL RNA

IIC4   293

ENCAPSIDATION OF RECOMBINANT AAV

TRANSFECT WC3 VECTOR CONTAINING PROMOTER AND GENE OF INTEREST AND HELPER AAV CONTAINING A 5KB LAMBDA FRAGMENT THAT SHOULD PROVIDE NONSTRUCTURAL PROTEINS FOR DNA REPLICATION AND STRUCTURAL PROTEINS FOR ENCAPSIDATION *IN TRANS*. SUPERINFECT WITH ADENOVIRUS OR HSVI

HARVEST VIRUS AT 40-48HRS, DISSOCIATE BY FREEZING/THAWING, SONICATE, HEAT INACTIVATE HELPER VIRUS

INFECT NEW CELL CULTURE WITH RECOMBINANT VIRAL STOCK (CHECK FOR ENCAPSIDATION OF rDNA BY :
- TRANSFER OF GENE ACTIVITY
- SOUTHERN BLOTS OF VIRAL DNA FOR INSERT)

DERIVATION OF THE CWRSVN PARENT PLASMID
INSERTION OF THE RSV LTR IN pWC3

CWR BASED VECTORS

CWR BASED VECTORS

ADENO-ASSOCIATED VIRUS (AAV)-BASED EUCARYOTIC VECTORS

This application is a continuation of application Ser. No. 07/752,899, filed Aug. 26, 1991, now abandoned, which is a continuation of U.S. Ser. No. 07/527,195, filed May 23, 1990, now abandoned.

BACKGROUND OF THE INVENTION

1. Technical Field

The present invention relates to adeno-associated virus (AAV)-based eucaryotic vectors and uses thereof. Such vectors, for example, may be utilized to down regulate any targeted viral or cellular gene whose sequence is known. Furthermore, the vectors may also be used to cause the expression of proteins.

The present invention specifically includes an adeno-associated (AAV)-based eucaryotic vector which confers intracellular resistance to human immunodeficiency virus, type 1 (HIV-1), and an adeno-associated (AAV)-based eucaryotic vector which confers intracellular resistance to herpes simplex, type 1 (HSV-1) infection.

2. Background Information

The acquired immunodeficiency syndrome (AIDS) is a chronic debilitating illness characterized by immunodeficiency and opportunistic infections of afflicted individuals. Human AIDS is caused by two members of the lentivirus subfamily of retroviruses, the human immunodeficiency viruses types 1 and 2 (HIV-1 and HIV-2). The natural course of HIV infection in humans is marked by a relentless progression towards end-stage disease over a period of years. Ultimately, high levels of HIV replication and overwhelming opportunistic infections lead to a fatal outcome in most patients. Current estimates indicate that over one million people in the United States may be infected with HIV-1. Thus, recent progress in antiretroviral chemotherapy notwithstanding, novel approaches to the treatment and prevention of AIDS are urgently needed.

Replication of the pathogenic lentivirus, human immunodeficiency virus (HIV-1) involves a highly complex and tightly regulated coordinate expression of virally encoded genes (Varmus (1988), Cullen et al., Cell 58:423–26 (1989) & Rabson). Following entry of the virus into the cell via cell surface receptors which include the helper T lymphocyte determinant CD4 and other as yet undetermined elements (Arthos et al. (1984), Delgleish et al. (1984) & Camerini et al. (1990)) the viral genome is uncoated and reverse transcribed into proviral DNA. Following translocation of the proviral DNA into the nucleus, transcription is initiated under the right cellular environment. Activation of transcription of the HIV genome is complex and highly regulated. Both cellular factors as well as virally encoded proteins regulate gene expression from the HIV long terminal repeat (LTR). The HIV LTR contains the target sequences for both constitutive and inducible host transcriptional activating factors such as SP1, NF1, TF IID and NK-KB (Cullen et al., supra.), the major transactivator of the HIV LTR is virally-encoded tat protein (Rice et al. (1989), Berkhout et al. (1989), Sodroski et al. (1985) & Arya et al. (1985)). Following initial activation of viral transcription, perhaps by cellular factors, the appearance of the multiple spliced early 2 kb species of viral mRNA which encode regulatory proteins tat, rev and nef is observed. Tat is a potent HIV LTR-specific transactivator which markedly increases transcription of all species of HIV messages including itself. The cis-acting target sequence of tat function, TAR, is present in the 5'untranslated leader of all HIV-1 messages and extends from bases 1 to 59 of HIV transcripts, with the sequences between bases 19 to 44 comprising the core TAR sequence. This region is involved in the formation of a stable stem loop structure which is recognized by tat in a sequence-specific and an orientation dependent-manner (Rice et al. (1989) & Berkhout et al. (1989)). This interaction is essential for expression of all HIV-encoded genes and subsequent viral replication. The action of tat results in the accumulation of viral transcripts by a complex mechanism of action, possibly by promoting RNA elongation and/or increasing the rate of initiation. The transition to the intermediate and late phases of HIV replication is mediated by rev, another regulatory protein encoded by the 2 kb early messages. Expression of rev results in the accumulation of singly spliced 4 kb messages encoding env and vif and full length message encoding gag and pol. Rev appears to increase transport of messages out of the nucleus into the cytoplasm for translation, feedback inhibiting itself. Like tat, rev recognizes a complex stable RNA secondary structure, called the rev responsive element (RRE), composed of several stems and loops and occurring within env coding sequences and present in the singly spliced and unspliced messages. The function of the regulatory protein nef is still controversial (Baltimore, Nature 335:395–96 (1988), Venk, & Cullen et al. Cell 58:423–26 (1989)). It has been suggested that it functions to downregulate HIV gene expression, thus promoting latency. Thus, there are several important regulatory elements in the HIV replication cycle which may function as efficient targets for antiviral therapy.

One novel strategy for use in the treatment and prevention of AIDS involves the concept of "intracellular immunization" whereby individual cells (perhaps stem cells) are rendered resistant to virus replication by the stable introduction of DNA sequences that are transcribed into antisense RNA or mRNA that encodes a protein with a dominant negative phenotype (Herskowitz, Nature 329:212–22 (1987) & Baltimore, Nature 335:395–96 (1988)). The effectiveness of dominant negative molecules in blocking target gene functions of impeding virus replication has been demonstrated in a number of different systems (Friedman et al., Nature 335:452–54 (1988), Malim et al., Cell 58:205–14 (1989) & Trono et al., Cell 59:113–20 (1989)). For virus replication in cell culture, much of the work to date has either involved transient expression systems or the exogenous administration of antisense synthetic oligonucleotides that do not confer permanent resistance to viral replication. To impart perpetual "intracellular immunity" to cells that are the targets for virus replication, it may be desirable to contrive a means for the intracellular synthesis of dominant negative molecules that are capable of interfering with critical steps in the virus life cycle. The feasibility of such a strategy depends on many factors including: (i) the ability to deliver and establish stable expression of DNA sequences within the desired cell population; (ii) the efficiency of expression within the target cell without cytotoxic effects; and, (iii) the true effectiveness of dominant negative molecules in reducing or abolishing the burden of infectious virus.

The capability to control (or prevent) HIV infection by the constitutive intracellular expression of molecules designed to inhibit HIV replication would represent a significant advance in the field of AIDS therapy. Thus, the present inventors have initiated efforts to develop a safe, feasible, and effective system for inserting DNA sequences into the host cell genome that might ultimately confer resistance to HIV replication.

Another virus, Herpes simplex virus (HSV), continues to be a major human pathogen which is associated with serious mucocutaneous and visceral infections, particularly in the neonate and immunocomprised host. Although acyclovir therapy has made a major impact upon the overall treatment of HSV infections, it is not curative, and acyclovir-resistant HSV strains are being reported with increasing frequency Marks et al., *Rev. Infect. Dis.* 11:474–76 (1989) & Sacks et al., *Ann. Intern. Med.* 111:893–99 (1989)). Thus, other methods are continually being sought to control HSV-1 replication and infection.

Antisense oligonucleotides targeted against areas of critical viral RNA transcripts including the 5'-untranslated region, splice sites, and the polyadenylation signal have demonstrated significant antiviral activities. Treatment of cells with methylphosphonate oligonucleotides targeted to the splice acceptor regions of immediate early (IE) genes ICP 22 and 47 of HSV-1, for example, has resulted in up to 5% inhibition of virus replication and DNA synthesis with minimal effects upon cellular metabolism (Smith et al., *Proc. Natl. Acad. Sci. USA,* 83:2878–91 (1986) & Kulka et al., *Proc. Natl, Acad. USA* 86:6868–72 (1989)). However, exogenously administered oligonucleotides require continuous administration to prevent HSV-1 reactivation, and are subject to degradation by cellular nucleases and the vicissitudes of cellular transport.

Herpes simplex virus replication entails a well orchestrated, regulated cascade in which a virion encapsidated, virus-encoded protein (VP16), in association with cellular DNA binding proteins, transactivates virus IE gene promotors. ICP4, an IE gene, is necessary for subsequent transactivation and regulated expression of early and late viral genes. Thus, the VP16 and ICP4 gene products play pivotal roles in HSV lytic infection, and mutations which inactivate them are generally lethal. Hence, they represent ideal targets for potential control of HSV-1 replication. A stable cell line constitutively expressing a carboxy-terminal truncated, non-effector (transdominant) form of VP16 has recently been shown to specifically inhibit HSV-1 replication by 20–40 fold in comparison to control cells. Baltimore has termed this modulation of cellular resistance to vital infection "intracellular immunization," and a number of groups have recently utilized similar methods of develop transdominant inhibitors of human immunodeficiency virus (HIV-1) regulatory proteins.

Adeno-associated virus (AAV), a parvovirus dependent upon adenovirus or herpes virus for full "lytic" infection (Buller et al., *J. Virol.* 40:241–47 (1981)), offers several advantages as a eucaryotic viral vector among which are lack of cytopathogenicity, wide host range, stability, clonability into bacterial plasmids allowing for easy manipulation, high frequency transduction, and high frequency integration into host cell DNA in the absence of helper virus coinfection (Lebkowski et al., *Mol. Cell. Biol.* 8:3988–96 (1988) & McLaughlin et al., *J. Virol.* 62:1963–2 (1988)). AAV may integrate site specifically into host cellular DNA (Kotin et al., *Proc. Nat'l. Acad. Sci., USA* 87:2211–15 (1990)). This feature would make it unique among currently used eucaryotic viral vectors, and would make it particularly useful as an antisense vector, as vector integration site influences the overall efficacy of antisense modulation of gene expression.

Site specific integration also greatly reduces the chance of insertional mutagenesis, which is known to occur with retroviral vectors. Other AAV vectors have been described, but none incorporate the features of the present vectors or were designed for the purposes described herein.

All patents and publications referred to herein are hereby incorporated by reference.

SUMMARY OF THE INVENTION

The present invention relates to adeno-associated virus (AAV)-based eucaryotic vectors and uses thereof. Such vectors, for example, may be used to down regulate any targeted viral or cellular gene whose sequence is known. Furthermore, the vectors may also be used in order to cause the expression of proteins.

More specifically, the invention includes an adeno-associated virus (AAV)-based eucaryotic vector, free of AAV coding sequences, comprising endogenous cis-active DNA sequences for AAV DNA replication, encapsidation and host cell integration, an endogenous AAV poly-adenylation signal, a promoter, and a heterologous DNA fragment wherein said promoter is operably linked to said DNA fragment which fragment is operably linked to said poly A signal. The DNA fragment may be present in the vector in the anti-sense or sense direction.

The invention also includes one or more cells transfected with the above vector and a culture containing these cells. Furthermore, the invention also includes the above vector wherein the DNA fragment within the vector encodes a foreign protein or a viral component.

Figure 1:
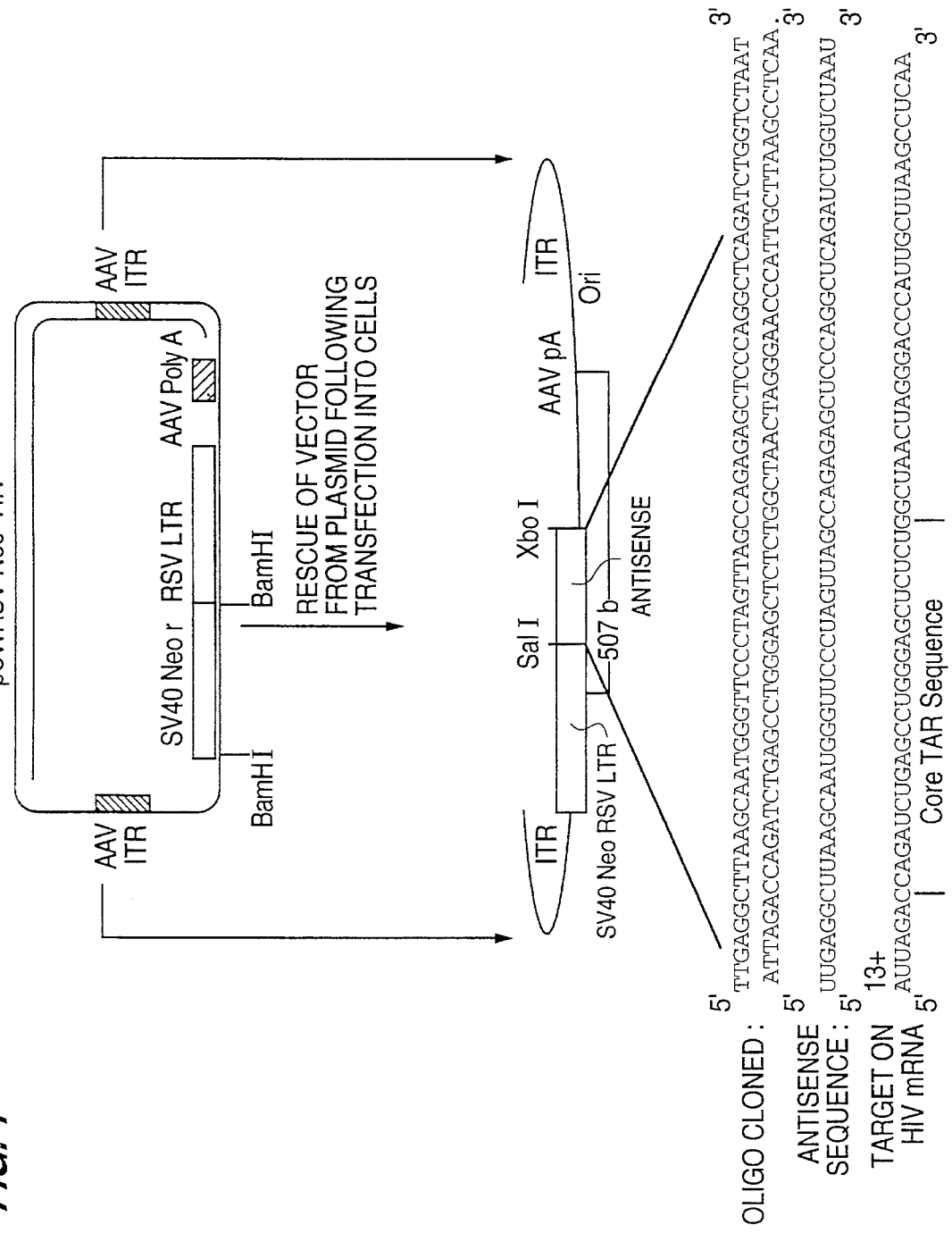
FIG. 1. A schematic representation of the expected events following transfection of a molecular clone of the antisense-encoding AAV vector.

This diagram shows the structure of the expected recombinant AAV genome following rescue from the plasmid, the sequence of the complementary oligodeoxynucleotides cloned into the vector, the predicted sequence of the antisense transcript and the target sequence in the 5' untranslated leader of HIV RNA including the core TAR sequence.

FIG. 2. The detection of the antisense transcript.

(A) The strategy for the PCR amplification of the antisense RNA. The transcript is predicted to be 507 bases long. Primer 1a is complementary to bases 481 to 507 of the transcript, and should be elongated by reverse transcription of the antisense RNA to cDNA. Primer 1b is complementary to bases 1 to 28 of the antisense transcript (from the Cap site within the RSV LTR). Elongation is mediated via Taq polymerase. The resulting double stranded cDNA copy of the antisense transcript is PCR amplified to yield the expected 507-base pair DNA band.

Ethidium bromide stained 1.5% agarose gel showing the products of PCR amplification as described in (A). A 507 bp band was detected in RNA from antisense clones Alpha 1 (lane 1), Alpha 2 (lane 2) and IIC4 (lane 4) but not from the parallel 293 cells (lane 3).

Demonstration that the PCR product was derived from an RNA template, RNA from clone IIC4 was treated with either RNase-free DNase (lane 2) or DNase-free RNase (lane 3) or left untreated (lane 1) prior to reverse transcription and PCR amplification as described in (A). The products were run on a 1.5% agarose gel and stained with ethidium bromide.

Hybridization of the PCR-amplified cDNA to an antisense-specific probe. The PCR amplified products from (B) were transferred onto nitrocellulose and hybridized with $^{32}$P-CTP-labelled T7-transcript complementary to the antisense sequence. The 507 bp band from clones Alpha 1 (lane 1), Alpha 2 (lane 2) and IIC4 (lane 4) hybridized with the probe. These bands did not hybridize with an irrelevant probe and neither did an irrelevant PCR amplified cDNA hybridize with the probe used here (data not shown).

FIG. 3. Inhibition of HIV LTR-directed gene expression in antisense-expressing clones.

(A) CAT activity under HIV LTR control in several antisense-expressing clones and parental 293 cells. A fluor diffusion CAT assay was performed on cell lysates harvested 48 hours post-transfection of $1 \times 10^6$ cells with 3 ug HIV LTR-CAT and 1ug HIV-LTR-Tat.

(B) A comparison of CAT expression under HIV LTR control versus E2 promoter control. CAT activity was measured in lysates of clones Alpha 1, Alpha 2, IIC4 and 293 cells 48 hours post-transfection with either 3 ug E2-CAT or 3 ug pBennCAT+1ug pAR.

(C) A comparison of CAT expression under HIV LTR control versus RSV LTR control. CAT activity was measured in lysates of clones Alpha 1 and 11C4 48 hours post-transfection with either 3 ug RSV-CAT or 3 ug pBennCAT+1ug pAR.

FIG. 4. Inhibition of HIV RNA accumulation in antisense-expressing clones.

(A) Total cellular RNA was harvested from clone 11C4 (lane 1) and 293 cells (lane 2) 4 days post-transfection with pHXB-2, an infectious molecular clone of HIV-1. RNA was pooled from 4 flasks of $2 \times 10^6$ cells each, transfected with 100 ng/flask of pHXB-2 and 3 ug E2-CAT as carrier DNA. 15 ug of RNA from each cell type was electrophoresed on a 1% agarose-formaldehyde gel in MOPS buffer, transferred to nitrocellulose and probed with a random primer labeled probe generated from 1475 bp fragment of pHXB-2 representing a sequence common to the 3' end of all HIV-1 messages, 9 kb, 4 kb and 2 kb species of HIV-1 messages are seen in RNA from 293 cells. CAT assays were performed with an aliquot of cell lysate to control for transfection efficiencies. Little variation in CAT activity from the two cell lines was seen indicating equivalent transfection efficiencies.

(B) A comparison of actin RNA in the above blot after stripping off the pHXB-2 probe. A random primer labeled actin probe generated from a 1.7 kb Pst 1 fragment of pActin was used.

(C) Ethidium bromide stain of the above RNA gel prior to transfer and hybridization. Equivalent amounts of 28S and 18S RNA are seen in both IIC4 (lane 1) and 293 (lane 2) RNA, indicating that equivalent amounts of RNA were loaded on the gel.

Figure 5:
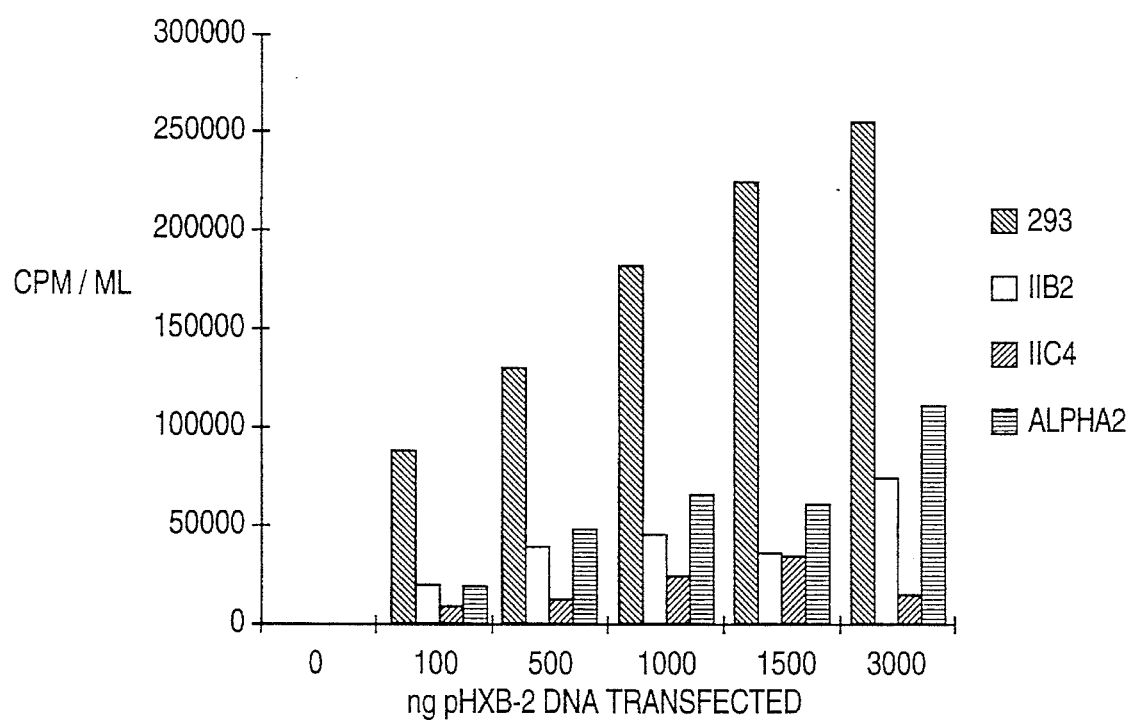

FIG. 5. Inhibition of HIV-1 replication in antisense-expressing clones.

$10^6$ cells from antisense clones IIB2, IIC4, and alpha 2 were transfected with 100 ng of pHXB-2 DNA (and 3 ug E2-CAT as carrier DNA). 2 ul of culture supernatant was assayed for reverse transcriptase activity. CAT assays performed on cell lyates at the end of the experiment revealed less than 10% variation between the clones indicating equivalent transfection efficiencies and a lack of toxicity as a result of antisense expression or neomycin resistance.

Figure 6:
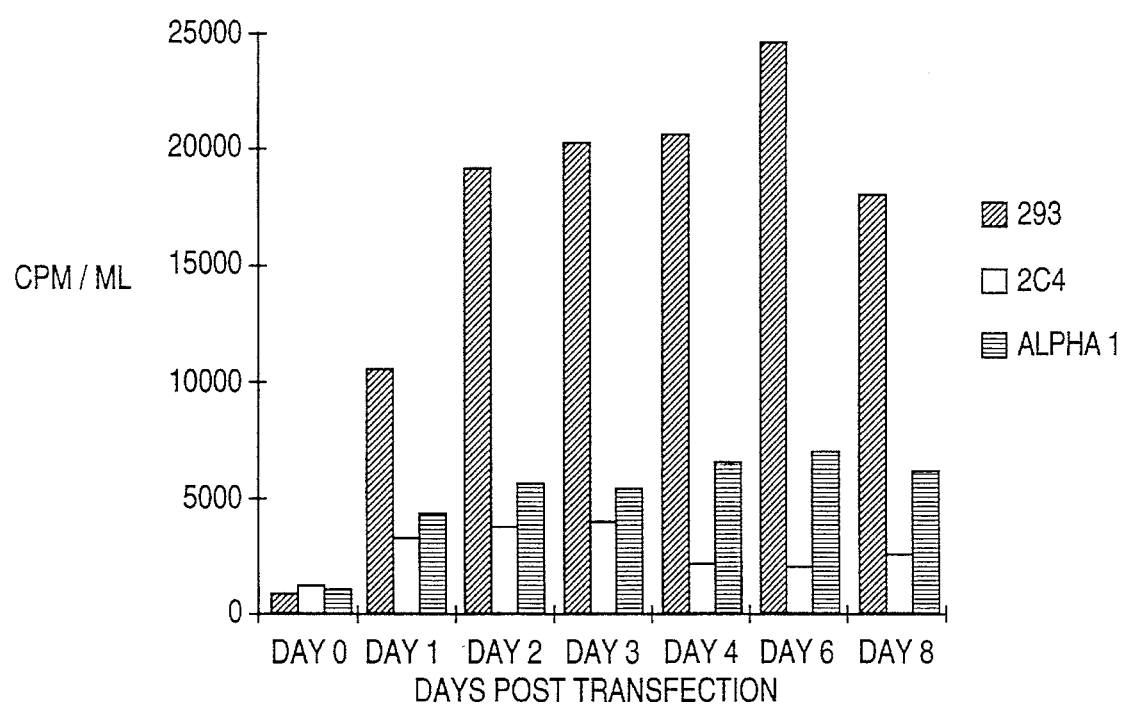

FIG. 6. Inhibition of HIV replication in antisense clones. Reverse transcriptase activity in clones IIC4 and Alpha 1 is compared with that from 293 cells following transfection of 100 ng pHXB-2 DNA daily after transfection.

Figure 7:
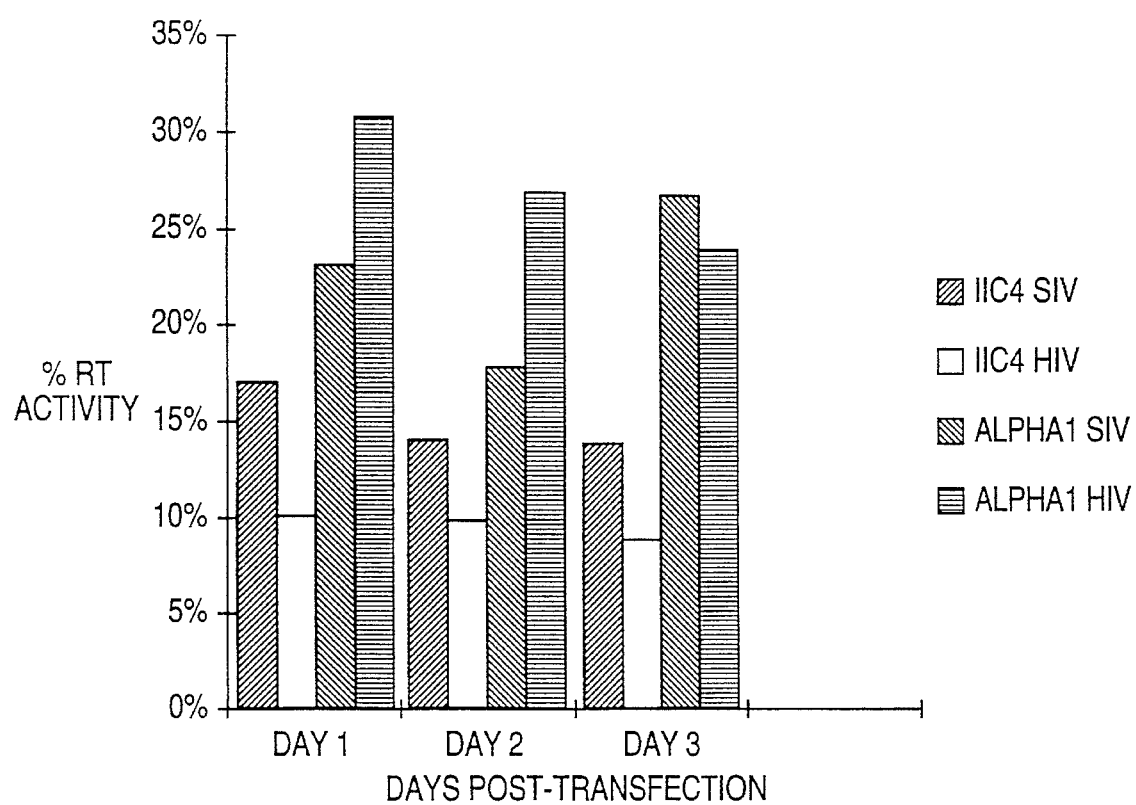

FIG. 7. A comparison of HIV-1 and $SIV_{mac}$ replication in antisense-expressing clones relative to parental 293 cells.

Reverse transcriptase activity from the culture supernatants of antisense clones Alpha 1 and IIC4 is expressed as a percentage of the same in 293 cells following transfection with 100 ng (and 3 ug E2-CAT as carrier) either pHXB-2 (HIV-1) or pSMMH41 ($SIV_{mac}$)/$2 \times 10^6$ cells. The relative ratios did not vary significantly with amount of transfected HIV or SIV plasmid DNA (ranging from 25 to 3000 ng of plasmid DNA/$1.5 \times 10^6$ cells).

Figure 8:
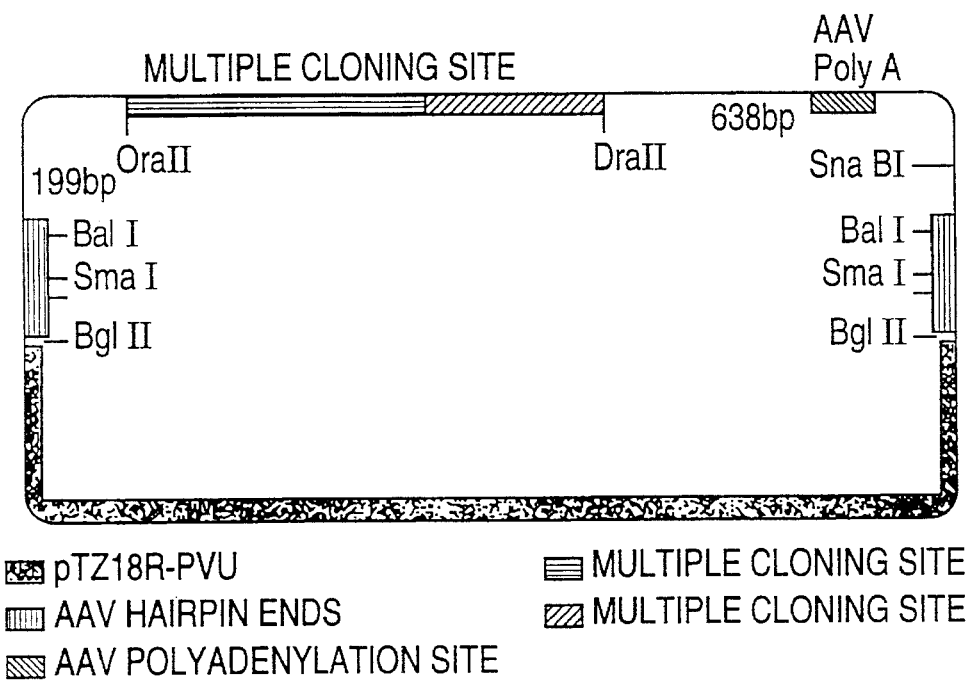

FIG. 8. Depiction of pWC3 revealing locations of BalI, SmaI, Bg III restriction sites as well as the location of retained AAV sequences.

Figure 9:
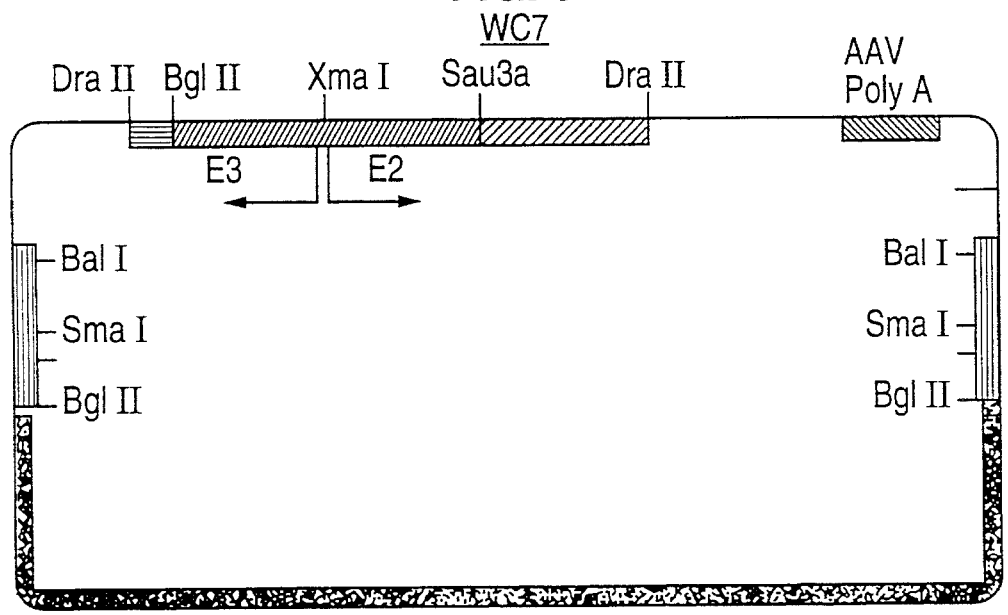

FIG. 9. Depiction of pWC7 a pWC3-based vector, into which the adenovirus type 5 E3/E2 promoter was inserted upstream of the endogenous AAV polyadenylation signal. The E3/E2 promoters are inducible by the E1a gene product which is constitutively produced in 293 cells. A synthetic oligonucleotide corresponding to the 5'-untranslated leader sequences of adenovirus E1a mRNA was inserted into this vector in an antisense orientation (to produce pWC7:E1a alpha). As E1a expression is necessary for the transformed phenotype of several cell lines, including the 293 cell line, transduction (infection) with this vector with expression of the antisense transcript abrogated E1a expression and reversed the transformed state. In addition, as E1a expression is necessary for adenovirus replication, abrogation of E1a expression would prevent adenoviral lytic cycle. Cells expressing an antisense to E1a appear to be relatively resistant to infection with adenovirus.

FIG. 10 (parts A and B). Construction of pWC3 (parent for AAV-based vectors):

1. pTZ18R (obtained from Pharmacia) was digested with PvuII to remove the endogenous T7 promoter and polylinker. A BglII linker was then inserted.

2. The entire genome of AAV was isolated as a BglII fragment from pAV1 (FIG. 10A) and inserted into the modified pTZ18R vector to yield pTZ18R-PvuIIB+AAV (FIG. 10B).

3. pTZ18R-PvuIIB+AAV was digested with DraII (AAV nucleotides 190 and 4034) and a synthetic oligonucleotide polylinker with BamHI,SacII,SacI,XbaI,HindIII, PvuII, EcoRI sites was placed between the AAV inverted terminal repeats. As the two AAV DraII sites are nonidentical, the polylinker could not be inserted in one orientation. The DraII digestion essentially removed all endogenous AAV promoters and coding sequences but left the AAV inverted terminal repeats (which contain the origin of replication, encapsidation signal, and sequences necessary for integration into host cellular DNA) and the polyadenylation signal intact.

Figure 11:
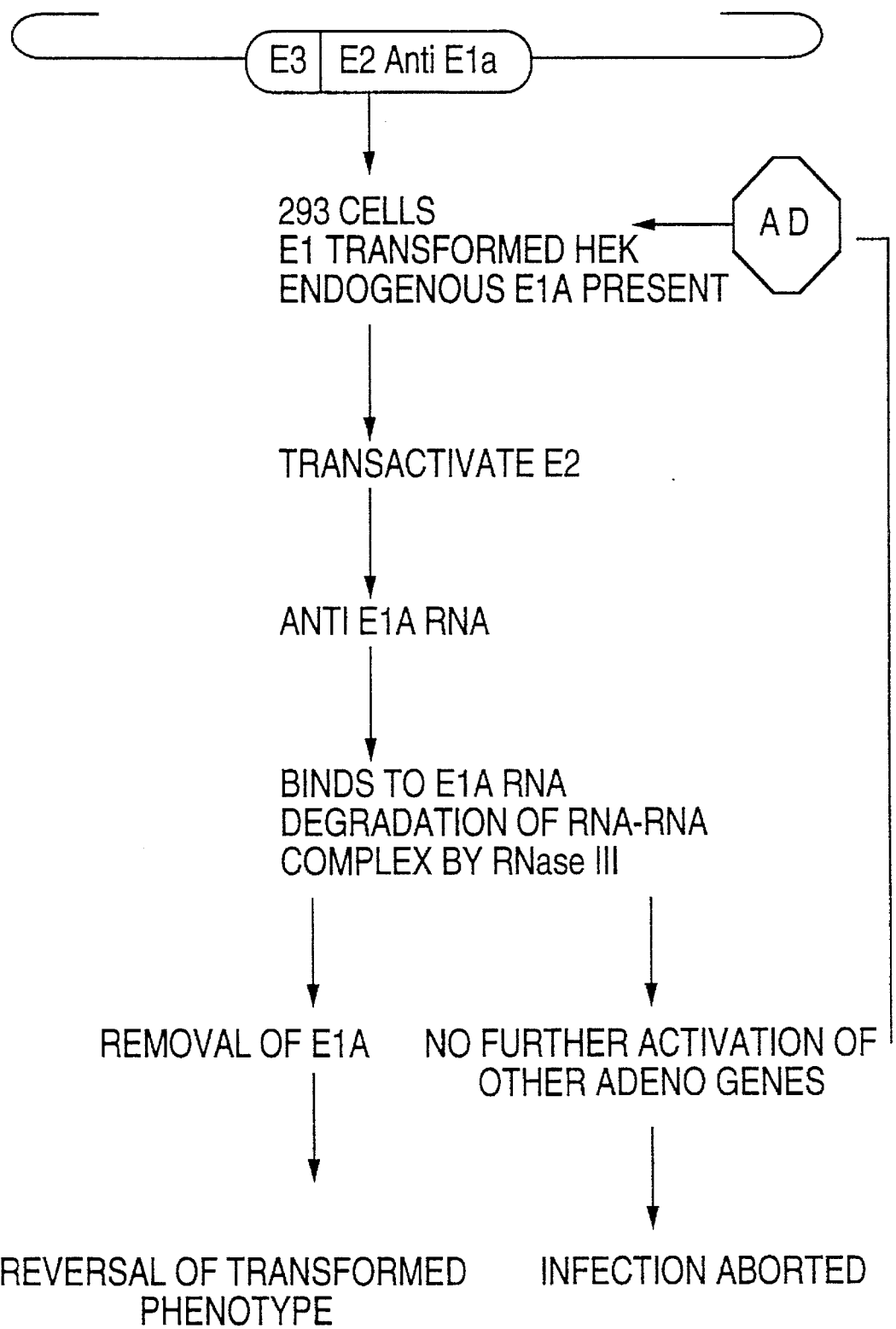

FIG. 11. Overall scheme of the interruption of E1a expression using the pWC7:E1a alpha vector and thereby reversing the transformed phenotype of 293 cells and interfering with the replicative cycle of adenovirus.

Figure 12:
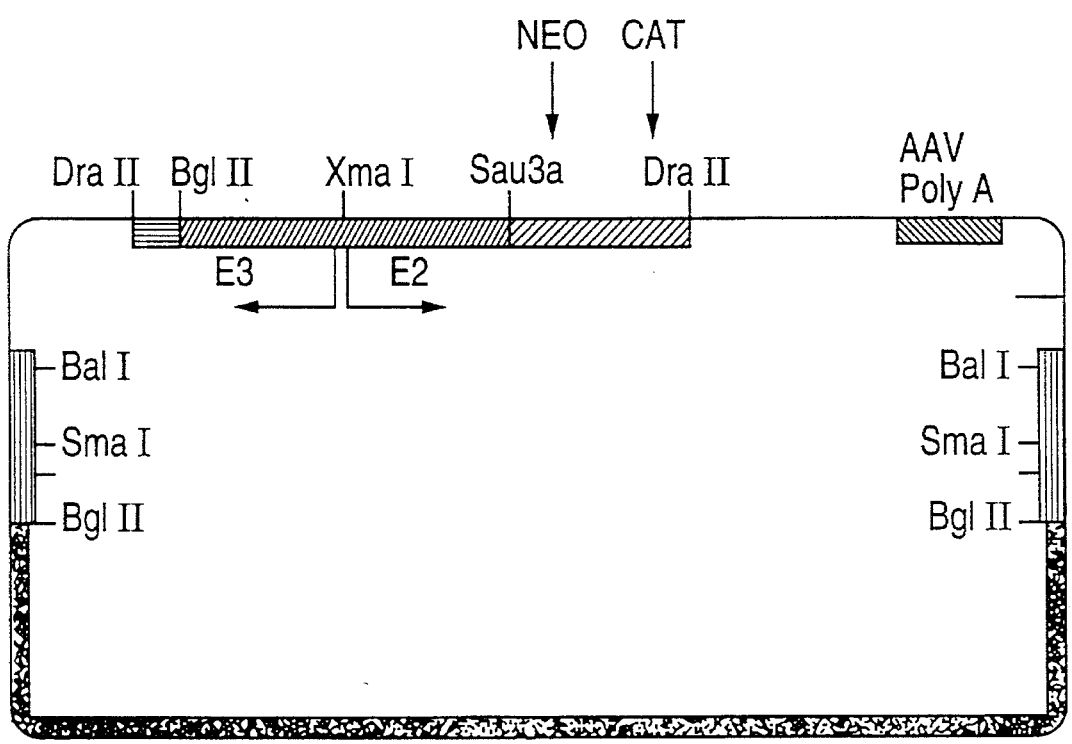

FIG. 12. Depiction of pWC7:neo and pWC7:cat in which the genes for neomycin resistance and chloramphenicol acetyl transferase (CAT) were inserted downstream of the adenovirus E2 promoter in pWC7. The vectors were used to test the efficacy of encapsidated recombinant AAV vectors in 293 cells. Neomycin resistance gene expression can be used to select cells which have been stably transformed by the recombinant vector using the cytocidal antibiotic G418 while CAT expression can be measured enzymatically in cellular extracts.

FIG. 13. Encapsidation of rAAV vectors:

AAV is a defective parvovirus which normally requires helper functions from another DNA virus, such as adenovirus or a herpes virus, for full "lytic" infection. The present vectors were so constructed to remove all endogenous AAV promoters. Thus, are also defective for AAV encoded functions which are necessary for AAV DNA replication and encapsidation into virus particles. However, these functions can be provided in trans by cotransfection of the recombinant AAV vectors with another plasmid encoding these functions into helper virus infected cells.

Figure 14:
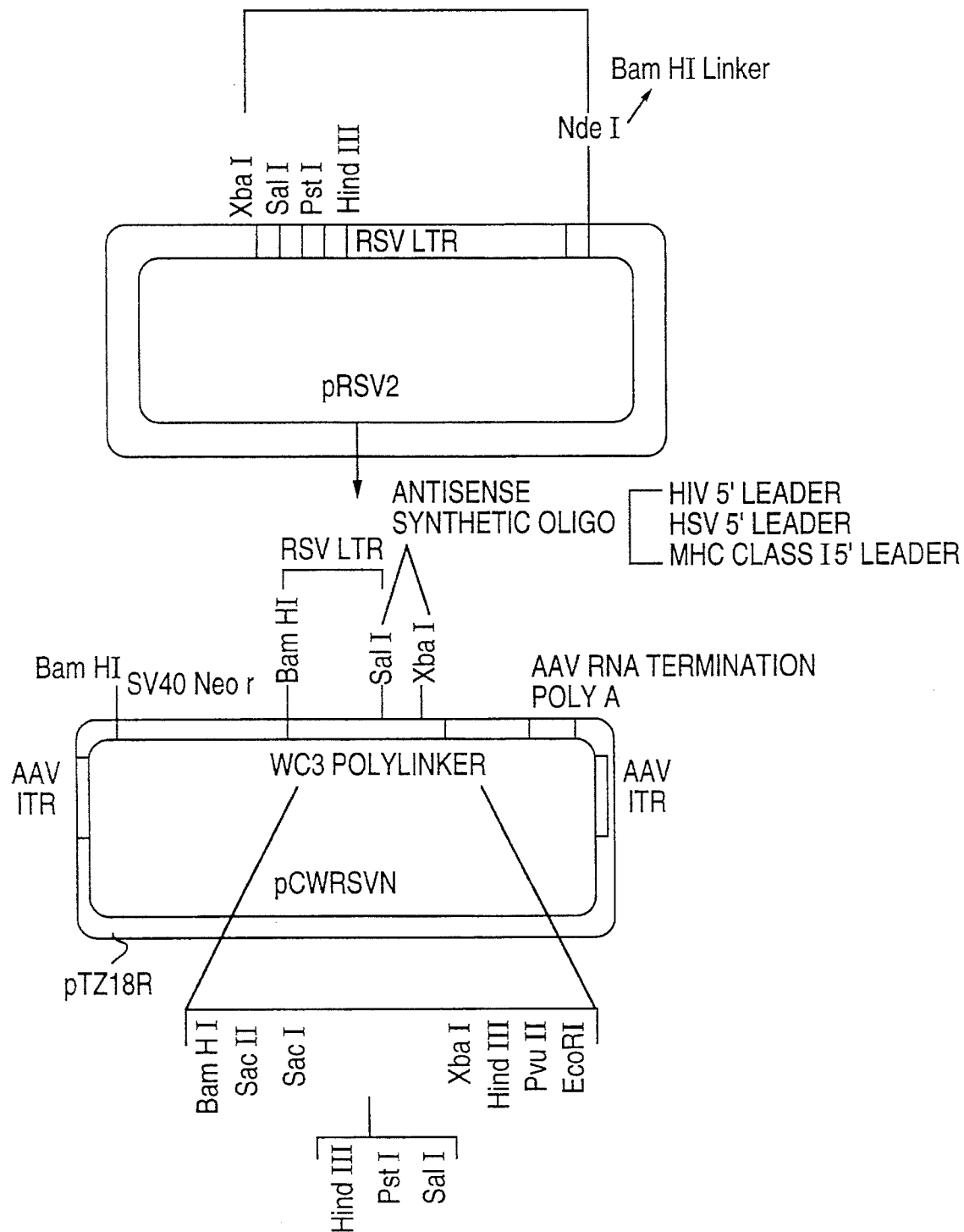

FIG. 14. Construction of pCWRSV (parent vector of HIV and HSV antisense vectors):

1. The pRSV.2 was digested with NdeI and filled in with Klenow fragment DNA polymerase and dNTPs. A BamHI linker was then added at this site.
2. The RSV (Rous sarcoma virus) promoter was isolated as a 580 pb XbaI-BamHI fragment and inserted into pWC3 in such a fashion that transcription is toward the endogenous AAV polyadenylation signal.
3. A neomycin resistance cassette in which the gene for neomycin resistance was inserted downstream of an SV40 promoter was inserted as a BamHI fragment to yield pCWRSV:SV40 neo.

Figure 15:
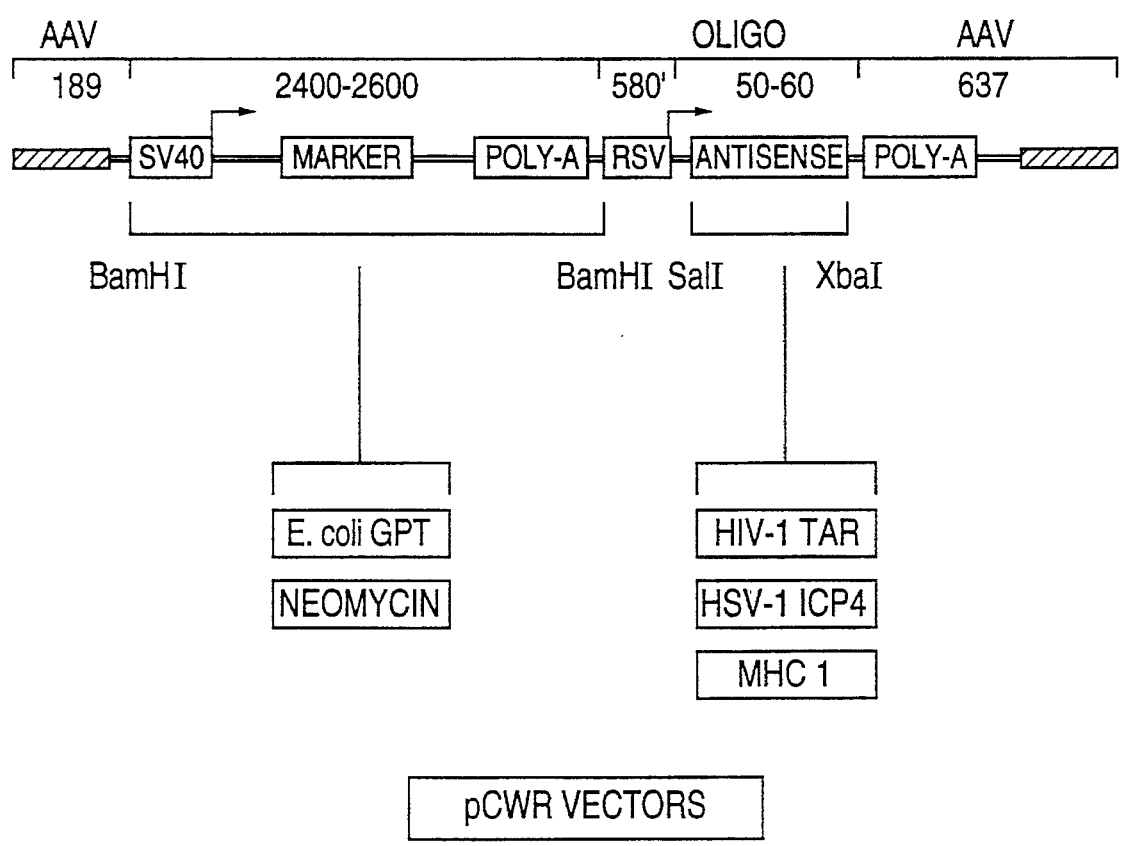

FIG. 15. General diagram of pCWRSV vectors:

Depicts the location of AAV sequences relative to the neomycin resistance cassette, the RSV promoter and the endogenous AAV polyadenylation signal. In addition, a mycophenolic acid resistance cassette (GPT) has been substituted for neomycin resistance in additional vectors. This diagram also depicts the insertion of synthetic oligonucleotides corresponding to the 5'-untranslated leader sequences of the HIV-1 TAR, HSV-1 ICP4, and murine major histocompatibility gene (MHC 1) RNA transcripts in antisense orientations.

Figure 16:
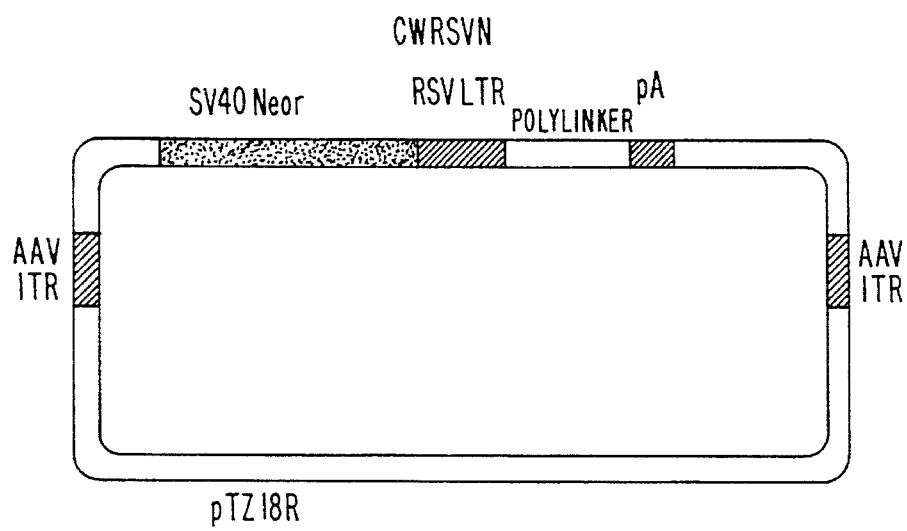

FIG. 16. HSV-1 Titer from cell supernatants:

Murine L929 cells (a fibroblastic cell line) were transduced (infected) with a recombinant AAV vector that constitutively expressed the antisense to herpes simplex virus (HSV-1) ICP4 as well as the gene for neomycin resistance. ICP4 is the major transactivator of HSV-1 and its expression is absolutely necessary for HSV-1 lytic infection. It was postulated that a cell which continuously expressed an antisense to ICP4 might be relatively resistant to HSV-1 infection. AG18 resistant cell line (presumably also expressing the antisense to ICP4) was isolated and examined for its ability to support HSV-1 infection.

Cells were infected at a multiplicity of infection of 0.1 (viron/cell), and cell supernatants were removed at the time of infection (TO) and daily. The amount of HSV-1 produced in these cell lines was determined by virus titration on Vero cells. As depicted in this figure there was a 2–3 log difference (>99% reduction) in the ability of HSV-1 to replicate in the cells expressing the antisense versus control cells (parental L929 cells or another neomycin selected cell line expression an irrelevant antisense).

Figure 17:
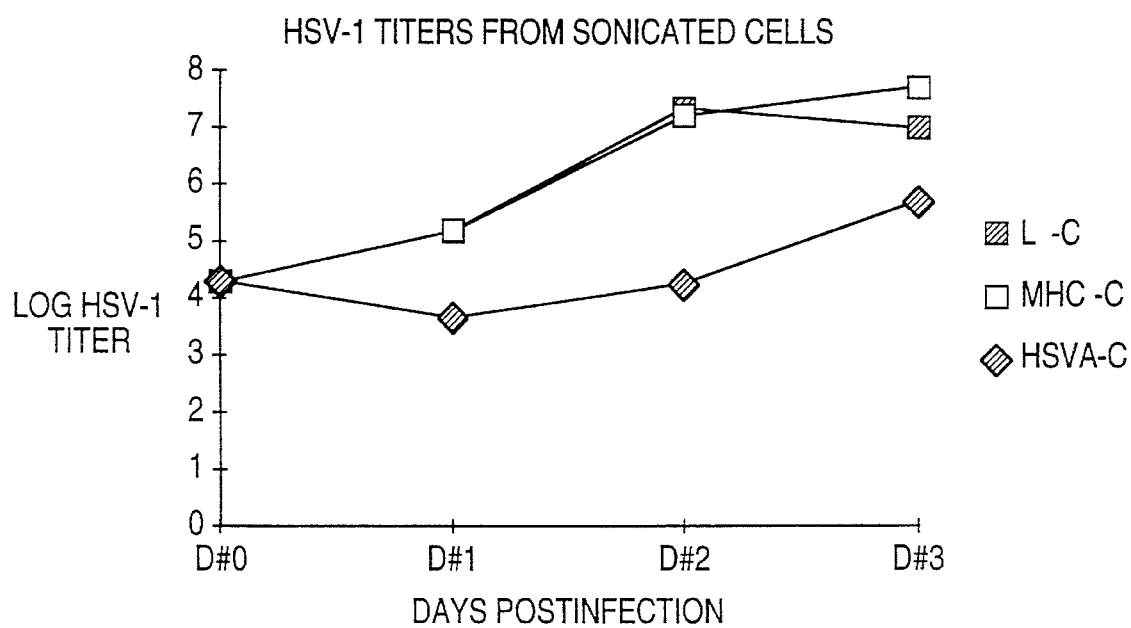

FIG. 17. HSV-1 titers from cell sonicates:

The amount of HSV-1 produced in cell sonicates was also examined to eliminate the possibility of a detect in virus release or the production of defective virions. As depicted in this figure, HSV-1 replication was also restricted.

Figure 18:
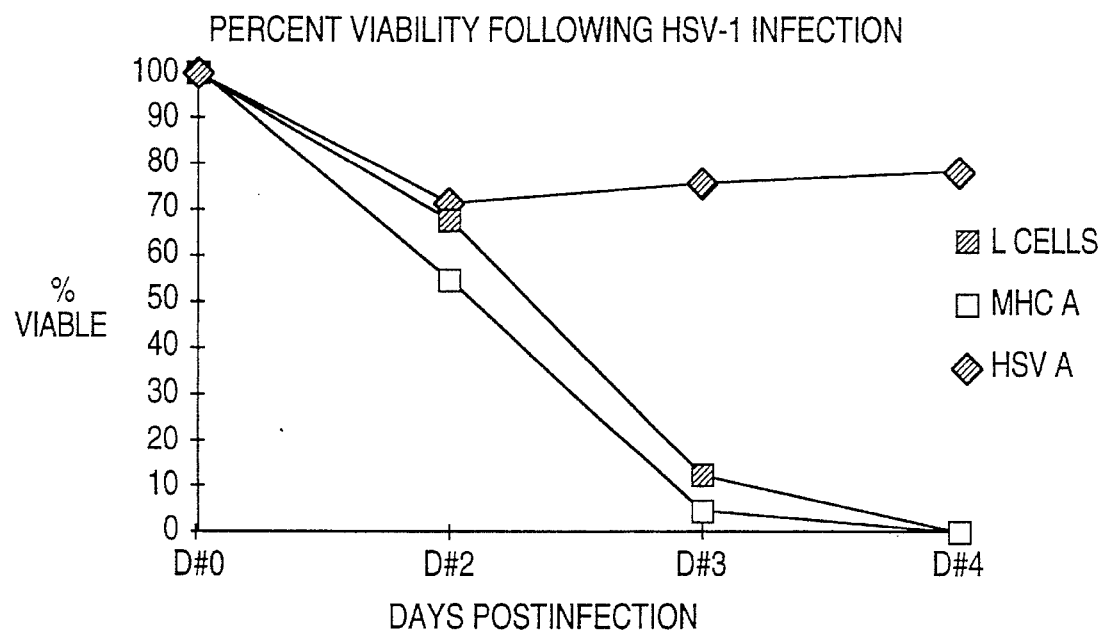

FIG. 18. Cell viability of HSV-1 infected cells:

To be effective as a potential form of therapy, it would be important to demonstrate that ICP4 antisense expressing cells would not only restrict HSV-1 replication but also be protected from the cytolytic effects of HSV-1. Cell viabilities, as determined by trypan blue dye exclusion, were determined after HSV-1 infection at an MOI of 0.1. As depicted in this figure, most of the control cells were dead by day 3 while 70–80% of the ICP4 antisense expression cell line were viable up to day 4.

Figure 19:
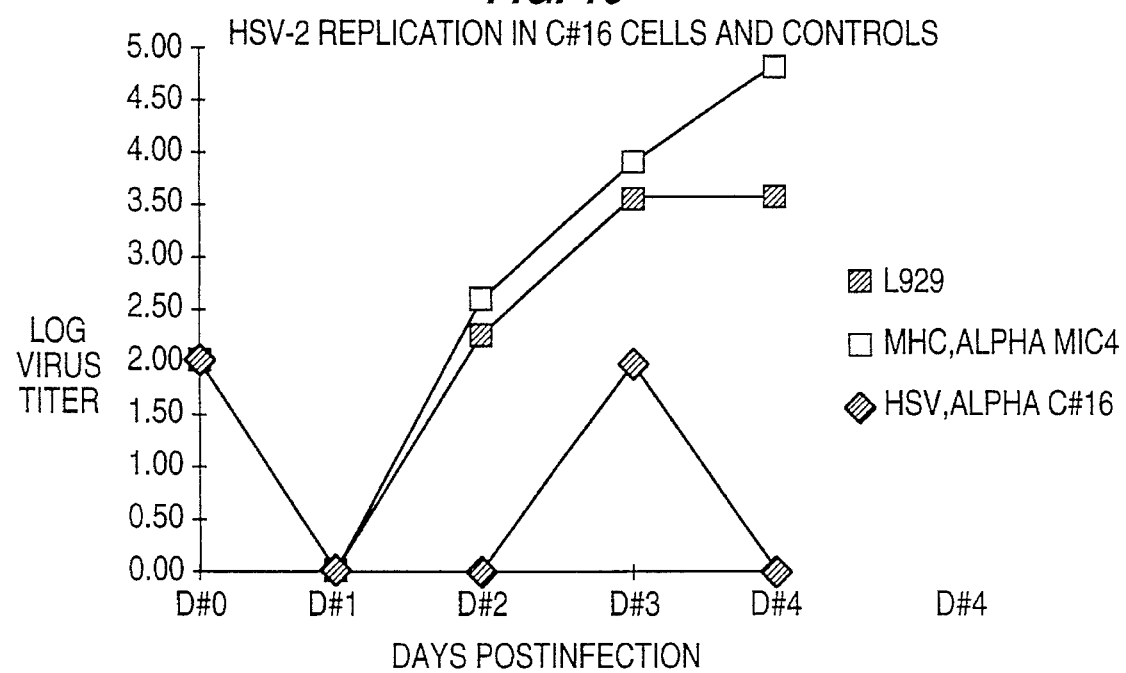
Figure 20:
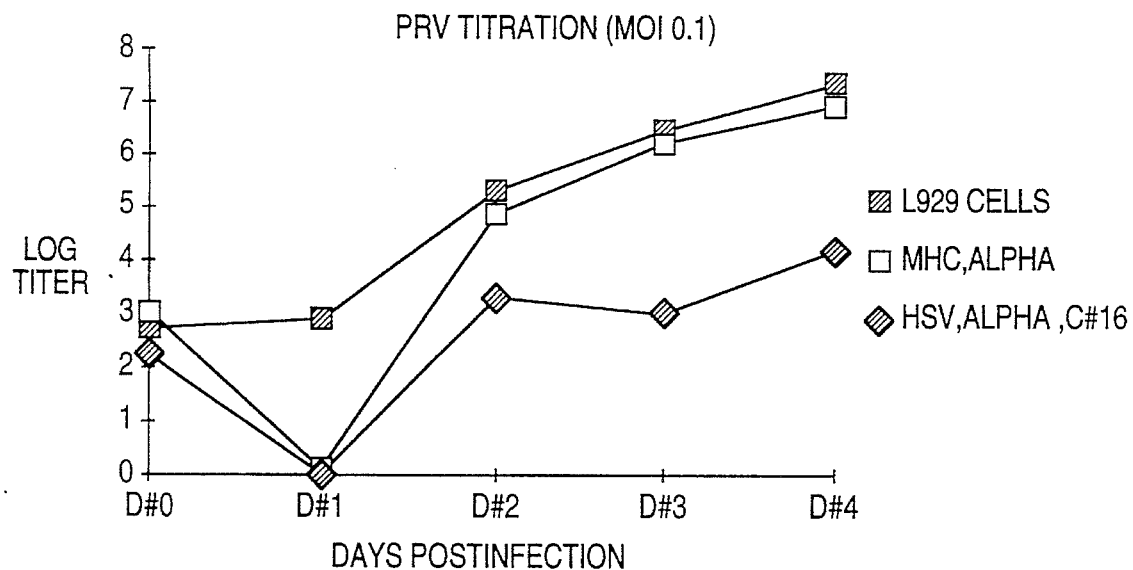
Figure 21:
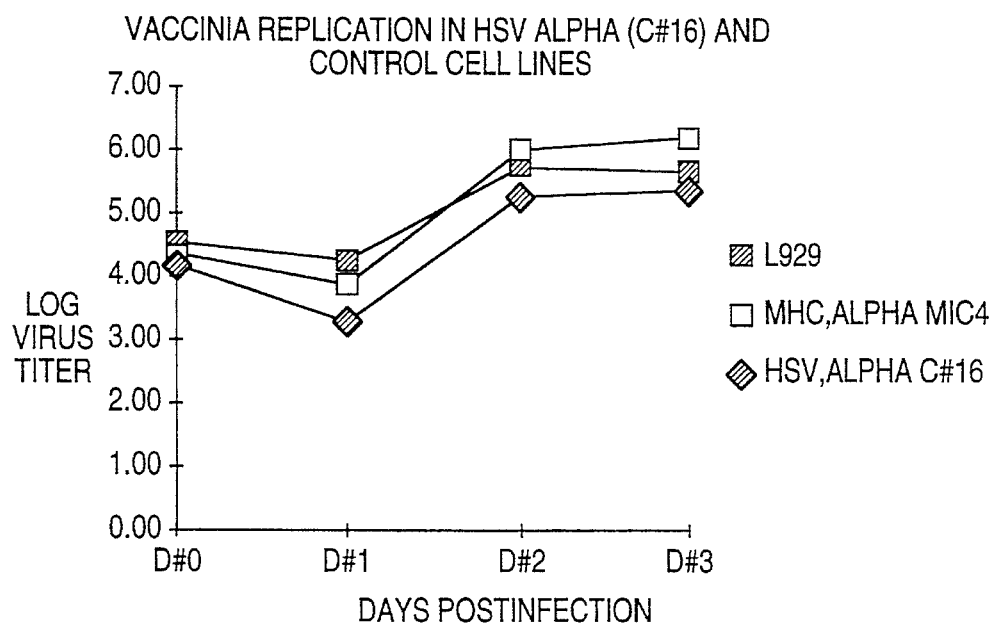

FIG. 19. Specificity of protection of ICP4 antisense expressing cells:

To determine the specificity of protection of IP4 antisense expression cell lines, cells were infected with other herpes viruses including herpes simplex type 2 (HSV-2), and pseudorabies virus (PRV), or with a totally different DNA virus, vaccinia virus at an MOI of 0.1 as shown in FIGS. 19–21, respectively. Results demonstrated that, the antisense expressing cell line was able to restrict replication of HSV-2 and PRV but not the unrelated virus vaccinia.

FIG. 20. PRV titration in HSV, Alpha (C #16) and control cell lines.

FIG. 21. Vaccinia replication in HSV, Alpha (C #16) and control cell lines.

Figure 22:
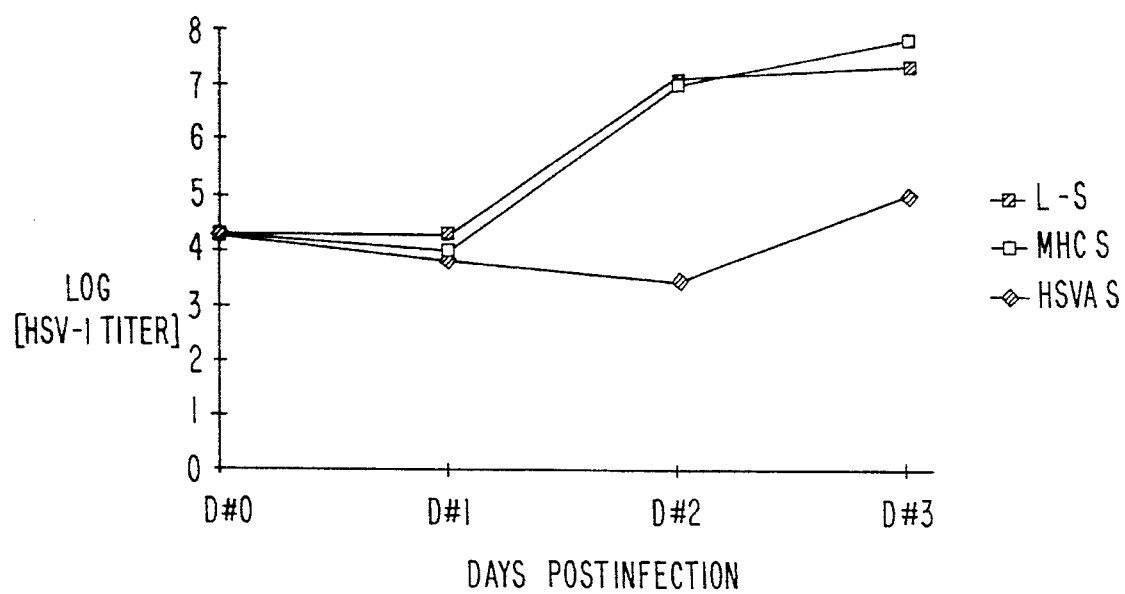

FIG. 22. Structure of the CWRSV:SN vector.

Figure 23:
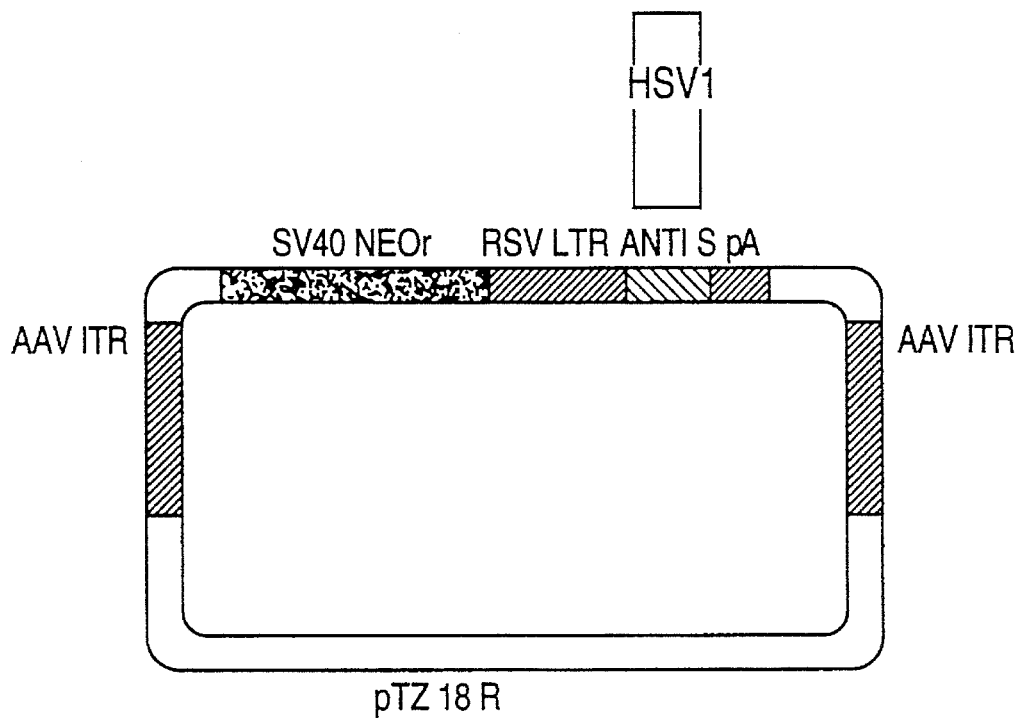

FIG. 23. Structure of the CWRSV:HSV-ASN vector.

Figure 24:
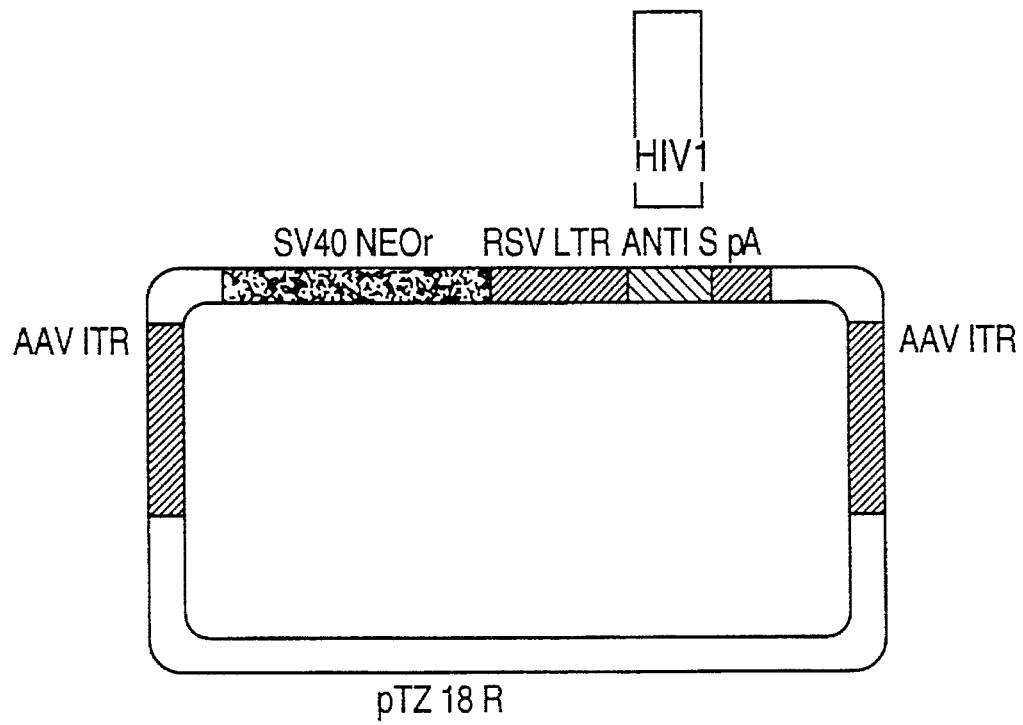

FIG. 24. Structure of the CWRSV:HIV-ASN vector.

DETAILED DESCRIPTION OF THE INVENTION

One embodiment of the present invention includes an adeno-associated virus (AAV)-based eucaryotic vector (termed CWRSV:HIV-ASN) in which all AAV coding sequences have been removed, but the cis-active DNA sequences necessary for AAV DNA replication, encapsidation, and host cell integration and the endogenous AAV polyadenylation signal have been retained. The HIV-1 TAR sequence is present in all known HIV-1 RNA transcripts, and is absolutely required for the transactivating effect of tat, the major HIV-1 encoded transactivating protein. Significant mutations in either the core TAR sequence or of the tat protein coding regions are lethal to the virus. The vector produces an antisense RNA molecule, under Rous sarcoma virus (RSV) promoter control, which is complementary to the 5'-noncoding region of the primary HIV-1 RNA transcript beginning at +13 to +75 nucleotides relative to the transcriptional start site and includes the core TAR sequence, thus inhibiting HIV-1 replication. Other promoters can be utilized. The sequence targeted is very highly conserved among different serotypes of HIV-1 so that cells expressing antisense RNA should be able to resist infection with different HIV-1 strains. The vector also contains the neomycin resistance gene under early SV40 promotor control, allowing for selection of vector carrying cell lines. This vector can be used to develop HIV-1 resistant cell lines, may be used in the development of HIV-1 resistant transgenic animals, and may be useful in treatment of HIV-1 infections in animal models of the disease or in Man. It has been cloned into a high copy number, PUC-based ampicillin resistant plasmid. The vector can be encapsidated by cotransfection with another plasmid containing the entire AAV genome minus the origin of replication (thus providing AAV rep and cap functions in trans) into adenovirus or herpes virus infected eucaryotic cells.

Basically, the AAV-based vector is used for the delivery of a DNA construct encoding an antisense RNA to the TAR region of the HIV-1 LTR. Clonal cell lines that constitutively express this RNA are potently refractory to HIV. They exhibit a significant and specific inhibition of HIV LTR directed gene function. Virus replication as well as the production of infectious particles in these clones is greatly reduced. The block of viral replication appears to reside at the level of HIV RNA accumulation. An encapsidated viral stock of the recombinant vector was also shown to transduce the dominant negative phenotype to an HIV-susceptible human T cell line in vitro.

The early Tat-TAR interactions were targeted for inhibition by a dominant negative antisense RNA. The virally-encoded Tat protein, is the major transactivator of the HIV LTR and promotes the accumulation of full length viral messages (Rice et al. (1989), Berkhout et al (1989), Dayton et al. (1986), Sodroski et al. (1985) & Arya et al. (1985)). TAR, the cis-acting target of Tat function, is present in the 5'-untranslated leader of all HIV-1 transcripts and forms a stable stem loop structure which is recognized by Tat in a sequence-specific, orientation dependent-manner (Rice et al. (1989) & Berkhout et al. (1989)). The interaction is essential for the efficient transcription of all HIV-encoded genes and mutations which interrupt it are lethal to the virus. Thus, interference at this level was expected to efficiently block all steps in viral replication.

The dominant negative phenotype of the antisense-expressing clones may be attributed to the formation of sense:antisense RNA hybrids. While the precise mechanisms Of antisense RNA mediated inhibition of gene function is still unclear, it is possible that the hybridization of the antisense RNA to TAR would lead to: 1) the disruption of the requisite stem loop structure of TAR and thus interference with Tat-TAR interactions, 2) the nuclear retention and accelerated degradation of all HIV messages, and 3) translational arrest by interference with ribosomal binding (Izant et al., Cell 36:1007–15 (1984), & Melton, Proc. Natl. Acad. Sci. USA 82:144–48 (1985)). The noncoding regions of messenger RNA, including the 5'-untranslated leader, splice junction sites and polyadenylation sites have indeed been reported to serve as efficient targets for antisense RNA-mediated inhibition of gene function. The proposed mode of action of antisense RNA suggests that the higher the molar ratio of antisense to sense transcripts, the greater the inhibitory effect. The number of intracellular copies of antisense transcripts may be manipulated either by increasing the number of integrated copies of the antisense gene, or by the use of a strong promoter. However, while the former is possible through the transduction of cells at a high multiplicity with the encapsidated viral vector, a strong constitutive promoter (RSV LTR) was chosen to direct the expression of multiple intracellular copies of the antisense RNA prior to the start of viral replication. The choice of an inducible promoter, perhaps even a tat-inducible one, may have been valuable if the expression of antisense RNA was toxic to the cells. However, no evidence of cellular toxicity was observed.

An AAV-based vector was chosen for the delivery of the antisense gene for several reasons. AAV is a nonpathogenic virus that can transduce cells of various lineages including hemopoietic, epithelial, and fibroblastic cells from different species (including simian and rodent cells (LaFace et al., Virol. 162:483–86 (1988)). Multiple copies of the recombinant vector integrate into cellular DNA in a tandem fashion following intracellular amplification making it highly efficient. AAV DNA does not exhibit inhibition of superinfection (McLaughlin et al., J. Virol. 62:1963–73(1988)) allowing possible transduction with several different vectors. AAV is also the only known human virus to integrate in a site-specific manner (Kotin et al., Virology 170:460–67 (1989), Kotin et al. Proc. Nat'l. Acad. Sci., USA 87:2211–15 (1990)), reducing the possibility of insertional mutagenesis inherent to other forms of gene transfer including retroviral vectors. The lack of homology between AAV and HIV greatly reduces the probability of the generation of altered viruses through homologous recombination. Therefore, AAV is an attractive virus for use as a vector in anti-retroviral gene therapy.

The present system, for the induction of intracellular resistance to HIV, fulfills the criteria of Baltimore's theory of intracellular immunization (Baltimore (1986)). The immunodeficiency aspect of AIDS is caused by the cytopathic effect of HIV of CD4 positive T helper cells. Also affected are cells of the monocyte-macrophage lineage which may act as reservoirs for the virus. Both of these hemopoietic cells renew themselves from a bone marrow stem cell population. AAV-based vectors similar to the one described here have been shown to infect bone marrow cells (LaFace et al., Virol. 162:483–86 (1988)). Therefore, AAV-based vectors may be used to deliver recombinant genes encoding dominant negative molecules to hemopoietic stem cells. The transduction properties of AAV based vectors described above, along with the use of a strong constitutive promoter, allows for a highly efficient expression of the dominant negative molecules within the target cells. The target of transdominant inhibition chosen, the 5' untranslated common leader including the TAR sequence, was shown to potently inhibit virus replication and the production of infectious virions. Furthermore, since the region targeted is highly conserved between different isolates of HIV-1, protection may be extended across several HIV serotypes. Similar vectors targeting multiple control steps in the viral replicative cycle in a combinatorial fashion may prove to be even more effective. Lastly, the expression of antisense RNA had no apparent toxicity in vitro. The treatment of bone marrow stem cells from HIV infected individuals in vitro, with a vector such as the one described here, followed by autologous transplantation of an expanded virus-resistant population could conceivably lead to restoration of immunocompetence following the repopulation of the immune system with HIV-resistant cells. Further studies are necessary to determine whether the expression of dominant negative molecules will have a deleterious effect on the differentiation of cells or whether the protected clones will proliferate sufficiently to reconstitute immunocompetence in an HIV-infected host. Nevertheless, the in vitro success of intracellular synthesis of dominant negative antisense RNA and mutant proteins (Malim et al, Cell 58:205–14 (1989), Green et al. Cell 58:215–23 (1989), Trono et al., Cell 59:113–20 (1989)) to interfere with viral gene function and replication is promising and may form the basis of antiretroviral gene therapy.

Another embodiment of the present invention involves an adeno-associated virus (AAV)-based eucaryotic vector (termed CWRSV:SN) in which all AAV coding sequences have been removed but the cis-active DNA sequences necessary for AAV DNA replication, encapsidation, and host cell integration and the endogenous AAV polyadenylation signal have been retained. A Rous sarcoma virus (RSV) promoter has been inserted upstream of the AAV poly-A signal, although other promoters can be used. It has been fully cloned into a high copy number, PUC-based ampicillin resistant plasmid. The vector is packaged by cotransfection with a plasmid containing the entire AAV coding sequences (providing AAV rep and cap functions in trans) but lacking the termini (and thus is ori negative) into cells previously infected with helper virus (adenoviruses or herpesviruses). Synthetic oligonucleotides or DNA fragments may be inserted in the sense or antisense orientation either to express proteins or to express antisense RNA for the purpose of downregulating or turning off targeted gene expression, for example, the adenoviral E1a gene. Thus, the viral vector is being utilized to transmit a gene into the cellular genome.

The vectors used to confer resistance to the HIV-1 and HSV virus, in the present invention, also function by down regulating gene expression.

The vector of the above embodiment also contains the neomycin resistance gene under early SV40 promotor control, allowing for selection of vector carrying cell lines.

The vectors of the present invention may also be used to reduce the expression of a wild-type protein. More specifically, the sequences of the vector may be altered such that the vector encodes the dominant negative protein of interest. This protein competes with the wild-type protein, and reduces expression of the wild-type gene, and consequently, the wild-type protein.

As noted above, the present vectors may also be used to cause the expression of proteins. The gene that encodes the protein of interest (for example, an enzyme, a hormone, or insulin) is inserted into a viral vector. An appropriate promotor is, of course, required. Furthermore, the parent vector is intially derived from an adeno-associated virus.

Cells are infected with the viral vector, and the gene that was inserted into the viral vector is expressed. Thus, the protein of interest is produced thereby, for example, compensating for a non-functional gene in a cell which renders the cell unable to produce the protein. A protein may also be produced which gives protective immunity by causing an immune response in the host. For example, an HIV envelope gene may be used to produce a protein which causes a T-cell or antibody immune response in the host. Thus, the vectors of the present invention may be used in the production of vaccines.

A further embodiment of the present invention involves an adeno-associated virus (AAV)-based eucaryotic vector (termed CWRSV:HSV-ASN in which all AAV coding sequences have been removed but the cis-active DNA sequences necessary for AAV DNA replication, encapsidation, and host cell integration and the endogenous AAV polyadenylation signal have been retained. The HSV ICP4 gene product is responsible for transactivating (turning on) other HSV encoded early and late genes and is, thus absolutely essential for full lytic HSV replication. This vector produces an antisense RNA molecule, under Rous sarcoma virus (RSV) promotor control, which is complementary to the 5'-noncoding region beginning 36 nucleotides upstream of the first translational "ATG" and extending 9 nucleotides downstream of the "ATG" of the ICP4 RNA message, thus inhibiting HSV-1 replication. Other promoters can be used. The vector also contains the neomycin resistance gene under early SV40 promotor control, allowing for selection of vector carrying cell lines. It can be used to develop HSV-1 resistant cell lines, and may be useful in the development of HSV resistant transgenic animals and possibly in the treatment of infections associated with HSV-1. It has been cloned into a high copy number, PUC-based ampicillin resistant plasmid. The vector can be encapsidated by cotransfection with another plasmid containing the entire AAV genome minus the origin of replication (thus providing AAV rep and cap functions in trans) into adenovirus of herpes virus infected eucaryotic cells.

More specifically, the adeno-associated virus vector termed CWRSV:HSV:SN) was constructed using standard cloning methods (Sambrook et al., in *Molecular Cloning*, a Lab. Manual, Second Edition (Cold Spring Harbor Laboratory, Cold Spring Harbor, N.Y. 1989)) in which almost all endogenous AAV coding regions were removed (nucleotides 189–4038)(rep, cap), while the endogenous AAV polyadenylation signal and cis-acting DNA sequences necessary for AAV DNA replication, encapsidation, and host cell integration were retained. A Rous sarcoma virus (RSV) promotor was inserted upstream of the AAV polyadenylation signal, as was a separate cassette in which the neomycin resistance gene was placed under SV40 early promotor control. Synthetic oligonucleotides corresponding to the DNA sequence of the 5'-RNA leader sequence 36 nucleotides upstream to 9 nucleotides downstream of the first coding "ATG" of the HSV-1 IPC4 gene transcript were inserted under RSV promotor control in the antisense orientation (McGeoch et al., *Nuc. Acids. Res.* 14:1727–45 (1986)). This vector, termed CWRSV:HSV-ASN, was encapsidated by calcium-phosphate mediated cotransfection with pTAAV, a plasmid containing the entire AAV DNA sequence minus the terminal repeats (nucleotides 119–4489) (ori), into Ad2 infected 293 cells. pTAAV provides AAV rep and cap functions in trans, but provides minimal DNA sequence overlap with CWRS-V:HSV-ASN, minimizing the generation of wild type AAV by homologous recombination. Cells were harvested after 48 hours post-transfection, lysed, contaminating Ad2 was heat inactivated, and CWRSV:HSV-ASN was used to transduce the murine cell line L929.

A stable, clonally derived G418-resistant cell line, termed C16, was isolated and tested for the expression of the appropriate antisense RNA as well as its ability to support HSV-1 replication. Standard Northern blot analysis of total RNA isolated from C16 cells using a $^{32}P$ labelled T7-transcript probe failed to demonstrate the presence of the antisense RNA. However, reverse transcription of total RNA isolated from these cells, in conjunction with polymerase chain reaction (PCR) amplification of the resulting DNA with antisense specific primers demonstrated the presence of an appropriately sized fragment which hybridized with the correct probe.

Serial light microscopic examinations following infection of C16 and control cells infected with HSV-1 at a multiplicity of infection (MOI) of 0.1 demonstrated a marked reduction in cytopathic effects (CPE) in the ICP4 antisense expressing line. Serial examination of HSV-1 supernatant plaque titers indicated that C16 was able to restrict HSV-1 replication by approximately 1000 fold by day 2 postinfection relative to control cells. This was also reflected in a 100 fold reduction in HSV-1 plaque titer in cellular lysates. In addition, overall cell viability was increased from 0% in the nonrestricting cell lines to about 70–75% in the HSV restricting cell line by day 4 postinfection. A similar level of inhibition of replication was also seen when herpes simplex type 2 (HSV-2)(MOI 0.1) or pseudorabies virus (PRV)(MOI 0.1), another herpes virus, were used to infect C16 cells. Vaccinia virus, an unrelated DNA virus, was able to replicate a similar extent in either C16 or control cells.

This high efficiency transducing vector system can be utilized to modulate resistance to HSV-1 infection. The advantages of such a system are several fold, and include the lack of pathogenicity, wide host range, high transduction frequencies, and possible site-specific integration of the AAV-based vector, and the ease in which specific genes can be targeted, simply by insertion of a appropriate synthetic oligonucleotide targeting an essential viral gene transcript 3'-to the RSV promoter. Similar vectors will be useful as tools to downregulate and dissect gene expression using either antisense transcripts or trans-dominant repressor. The present inventors are currently investigating the induction of "intracellular immunization" to several diverse viruses by targeting known essential genes.

The vectors may be utilized to treat patients suffering from viral diseases using vectors provided in the manner taught herein and exemplified specifically for herpes simplex virus and for AIDs in the following manner:

For example, bone marrow cells are removed from the patient. The cells are then infected with the vector. The infected cells are then introduced into the blood stream (or the bone marrow) of the affected individual by infusion, injection, or by any method which will allow the transfected cells to be reintroduced into the body. This method of utilizing the vector could be applied to the treatment of any viral infection.

With regard to the use of the vector in the treatment of a protein deficiency, a sample of the patient cells could be removed, transfected with the vector, and the transfected cells could then be introduced into the patient by an appropriate means such as by infusion or injection. Furthermore, it may be possible to simply administer the vector alone. It is important to note that the vectors could utilized in the treatment of any condition involving a protein deficiency The present vectors can also be used to target genes involved in neoplastic transformation of cells. For example, the vectors can be used to down regulate the adenoviral E1a gene which has been shown to be involved in retinoblastomagenesis. Using similar vectors encoding antisense RNA or the expression of dominant negative proteins, the vectors can be used to down regulate, for example, the Papilloma virus which has been implicated in venereal warts and cervical cancer. The down regulation of specific transforming genes should result in the reversion of the cancer cells to a normal phenotype.

Moreover, the vectors of the present invention can be modified to target major histocompatibility genes which are involved in graft rejection. More specifically, the down regulation of the class I genes will result in a non-rejection of tissue transplants. Down regulation of class I genes may be used to modulate immune responses such as the responses occurring in autoimmune diseases or in allergic reactions.

Additionally, the parent vector of the present invention can be modified to target SIV, the simian equivalent of HIV-1. The efficacy of the vector can be tested in the monkey model of AIDS.

The present invention can be illustrated by the use of the following non-limiting examples.

EXAMPLE 1

Vector Construction, Encapsidation and Derivation of Clonal Cell Lines

The vector used in this study was constructed by removing all endogenous promoters and protein coding sequences from an infectious molecular clone of AAV (FIG. 1). These sequences were replaced by the Rous sarcoma virus (RSV) LTR, a cloning site polylinker, and a cassette containing the neomycin resistance gene under the control of the SV40 early promoter. Complementary synthetic oligodeoxynucleotides spanning bases +13 to +75 (+1 is the RNA cap site) of the HIV-1 LTR were cloned into the polylinker immediately downstream of the RSV LTR. The predicted RNA transcript would be complementary to the 5' untranslated leader sequence (including TAR) common to all HIV transcripts.

Figure 10A:
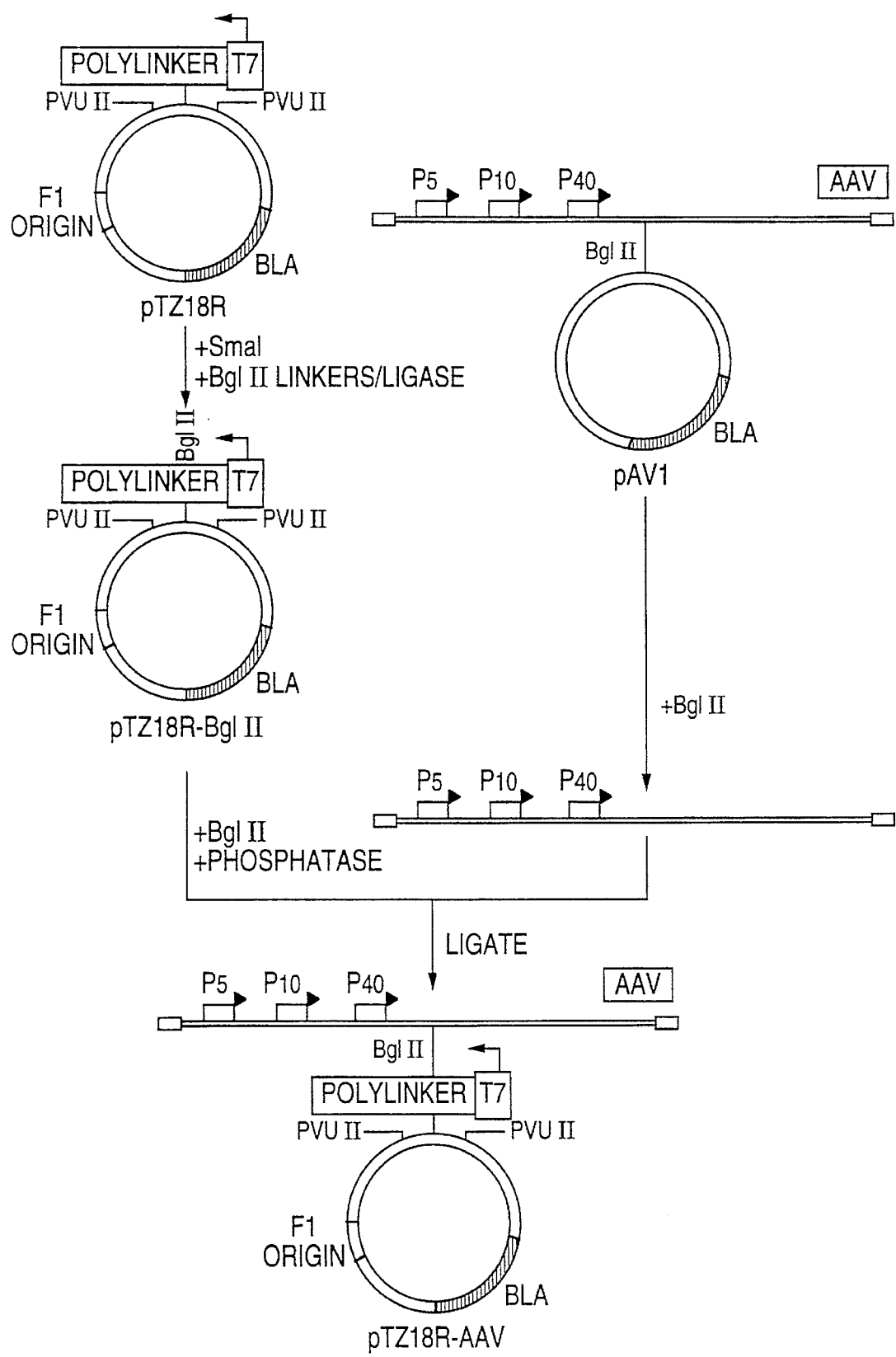
Figure 10B:
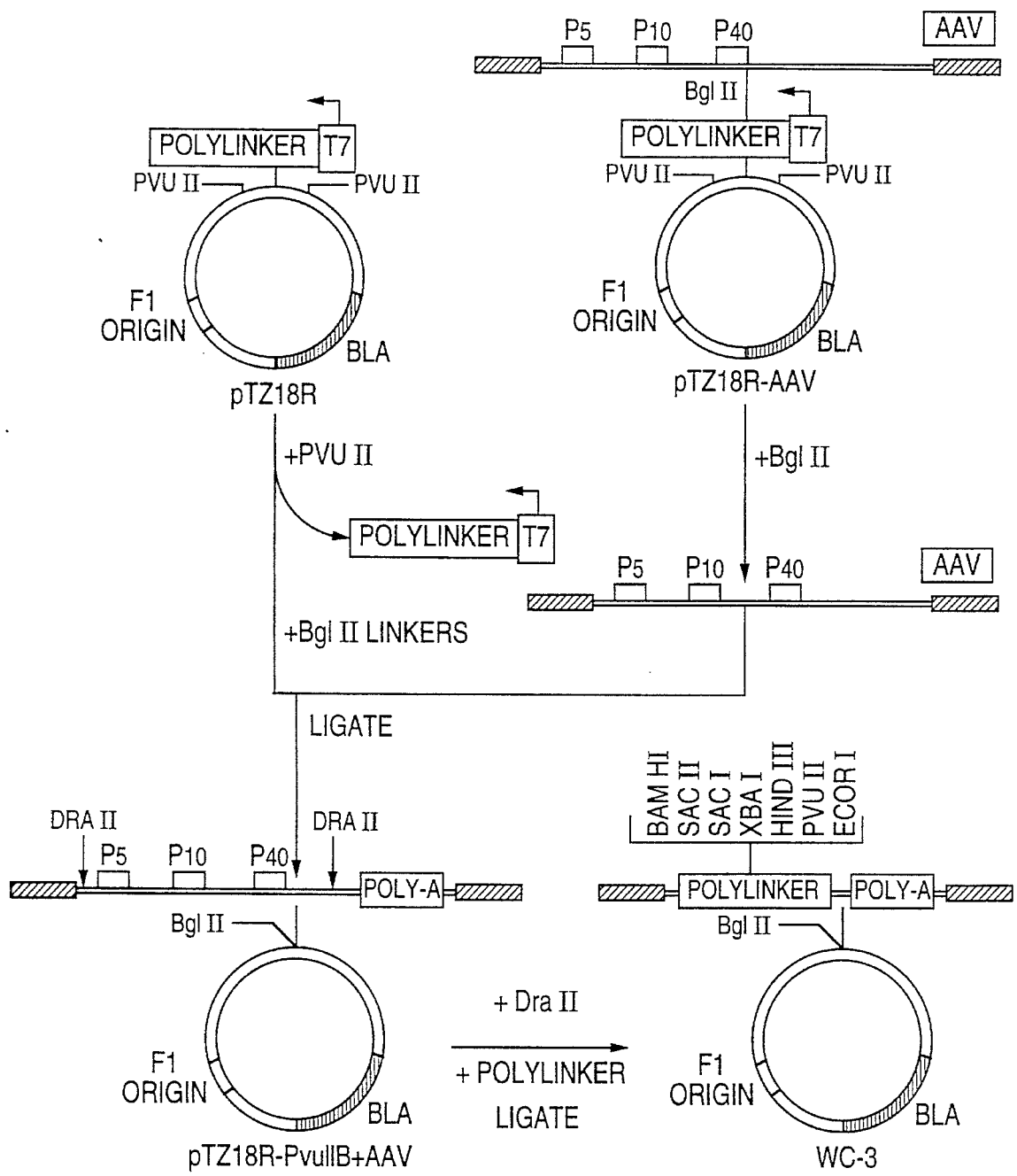

More specifically, the AAV based antisense vector was derived from the infectious molecular clone pTZ18R-AAV, generated by cloning the complete AAV genome from pAV1 via Bgl II linkers into the Sma 1 site of pTZ18 (Pharmacia) as shown in FIG. 10A. Following removal of DraII fragments (base 190 to base 4034 of the AAV genome), complementary synthetic oligonucleotides containing multiple cloning sites was inserted and the vector was ligated shut. This vector, pWC3 formed the parent vector for the AAV-based expression system. The RSV LTR obtained from PRSV.2 was directionally cloned into the multiple cloning site of pWC3 (pCWRSV). Complementary synthetic oligonucleotides corresponding to the sense sequence of bases +13 to +75 of HIV-1 MRNA were directionally cloned behind the RSV LTR. A neomycin resistance cassette containing the neomycin resistance gene under SV40 promoter control was excised as a Bam H1 fragment from the plasmid pMAM-LUC (Clontech) and inserted upstream to the RSV LTR. The resulting plasmid is called pCWRSV-HIVAlpha-Neo. The integrity of the AAV inverted terminal repeats was checked after each cloning step by digestion with Sma 1 and Bal 1. All cloning procedures were carried out under standard conditions (Sambrook et al., *Molec. Cloning: A Lab. Manual* (Cold Spring Harbor, N.Y.: Cold Spring Harbor Lab. (1989)).

Generally speaking, AAV is a single-stranded replication-defective DNA virus (parvovirus) that contains a 4.6 kb genome with palindromic inverted terminal repeats (ITR). Coinfection with a helper virus (such as adenovirus or herpes simplex virus) is required for productive infection. Importantly, molecular clones of the AAV genome are infectious following transfection into helper-virus infected cells. AAV vectors have high transduction frequencies, and in the absence of helper virus, integrate via the ITRs in a site-specific manner into the telomeric region of chromosome 19 (Kotin et al. *Virology* 170:460–67 (1989) & Kotin et al. *Proc. Natl. Acad. Sci. USA* 87:2211–15 (1990)). Thus, AAV vectors are suitable vehicles for the introduction of foreign DNA sequences into host cells.

Encapsidation of the recombinant vector was carried out by calcium phosphate cotransfection of pCWRSV-HIVAlpha-Neo with pTAAV (containing base to base of the AAV genome) (CellPhect, Pharmacia, N.J.) into helper virus-infected 293 or HeLa cells. pTAAV contains only minimal regions of homology with pCWRSV-HIVAlpha-NEO and therefore should not compete for encapsidation into AAV virions and minimizes recombinantional events which generate wild type AAV.

A human embryonic kidney cell line transformed by the adenovirus type 5 E1A and E1B genes (293 cells) was transfected with the vector construct described above, and G418 resistant colonies were harvested and propagated. Selected clones were subjected to the analyses described below.

EXAMPLE 2

Construction of Other Plasmids

RSV-CAT was generated by the insertion of the CAT gene at the Hind III site in pCWRSV. E2-CAT was generated by cloning a Sau 3a fragment from the plasmid pKCAT23 containing the adenovirus 5 E2/E3 promoters, into pWC3. The CAT gene was cloned as a Hind III fragment downstream from the E2 promoter. In both RSV-CAT and E2-CAT, the endogenous AAV polyadenylation signal was utilized for expression.

EXAMPLE 3

Transfection, Transduction and Derivation of Cell Lines 293 cells and all the derived clones were maintained in Eagle's minimum essential medium without calcium or magnesium salts, supplemented with 10% fetal calf serum. H9 cells were grown in RPMI containing 10% fetal calf serum. Neomycin-resistant cells were grown in media containing G418 (GIBCO) at an active concentration of 400 ug/ml. All transfections were carried out on semi-confluent monolayers of cells using the Cellphect kit (Pharmacia) (Graham and van der Eb, *Virology,* 52:456 (1973)). For the CAT assays, 3 ug of pBennCAT and 1 ug of pAR for HIV-CAT or 3 ug of RSV-CAT or E2-CAT were used. For transfections of pHXB-2 and pSMMH41, varying amounts of DNA ranging from 10 ng to 3000 ng were used. 3000 ng of E2-CAT was used as carrier DNA and as an indicator to determine transfection efficiencies. The cells were subjected to glycerol shock at 4 to 6 hours post transfection with 20% glycerol in phosphate-buffered saline for 2 minutes and assayed for various parameters at different times post transfection.

Antisense clones were derived following transfection of $2\times10^6$ cells at 80–90% confluency with 10 ug of pCWRSV-HIVAlpha-Neo. G418 (GIBCO) selection was performed at 48 hours post-transfection. Individual clones were picked and expanded for analysis by standard methods (Mulligan and Berg, 1980).

$2\times10^6$ H9 cells were transduced with encapsidated CWRSV-HIVAlpha-Neo at an MOI of approximately $5\times10^{-4}$ and selected with G418 at 400 mg/ml. Cells were tested for inhibition of HIV replication after 2 months of selection in G418.

EXAMPLE 4

RNA Analysis of Clonal Cellular Expression of the Predicted Antisense RNA Transcript Total cellular RNA was harvested from the parental 293 and several G418-resistant clonal cell lines predicted to be expressing antisense RNA. Specific antisense RNA transcripts were not detected in direct RNA blots (data not shown); these results are consistent with the findings of other investigators who were unable to directly demonstrate the presence of antisense RNA species. The inability to detect the predicted transcripts by conventional RNA blots may be related to rapid intracellular degradation of the transcripts, low level expression, or both. Therefore, a more sensitive detection method was devised based on polymerase chain reaction (PCR) amplification of RNA. As shown in FIG. 2, a product of the appropriate size (507 bp) from total cellular RNA, only from antisense expressing clones, was amplified. It was established that the template for amplification was RNA and not DNA. Furthermore, the product hybridized with HIV antisense specific RNA probes. Thus, these data demonstrated the presence of the predicted antisense RNA transcript in the G418-resistant clonal cell lines.

EXAMPLE 5

Analysis of HIV RNA Accumulation in Antisense Expressions Clonal Cell Lines

Total RNA extracted by the guanidinum isothiocyanate method from cells transfected with 100 ng pHXB-2 or pSMMH41 on day 4 post-transfection was capillary blotted onto supported nitrocellulose (Schleicher and Schuell) following electrophoresis in a 1% agarose gel in 0.66M formaldehyde in MOPS buffer by standard method (Battye). The blots were probed with random primer labeled probes synthesized from a 1475 base Hind III fragment (bases 8141 to 9615 of the HXB genome) from the 3' of pHXB-2 which includes sequences common to the 3' portion of all HIV transcripts. A 1.7 kb Pst 1 fragment from pActin was used to generate an actin-specific probe to control for the amount of RNA loaded in each well. Hybridization and washes were performed under standard conditions. PCR amplification of the antisense cDNA was carried out for 30 cycles with Taq polymerase (Perkin Elmer) under standard conditions. Southern blots of PCR amplified cDNA from antisense clones was probed with a 32P-CTP labeled RNA probe generated as a run-off transcript from a plasmid which had the antisense oligonucleotides behind a T7 promoter.

EXAMPLE 6

Figure 3A:
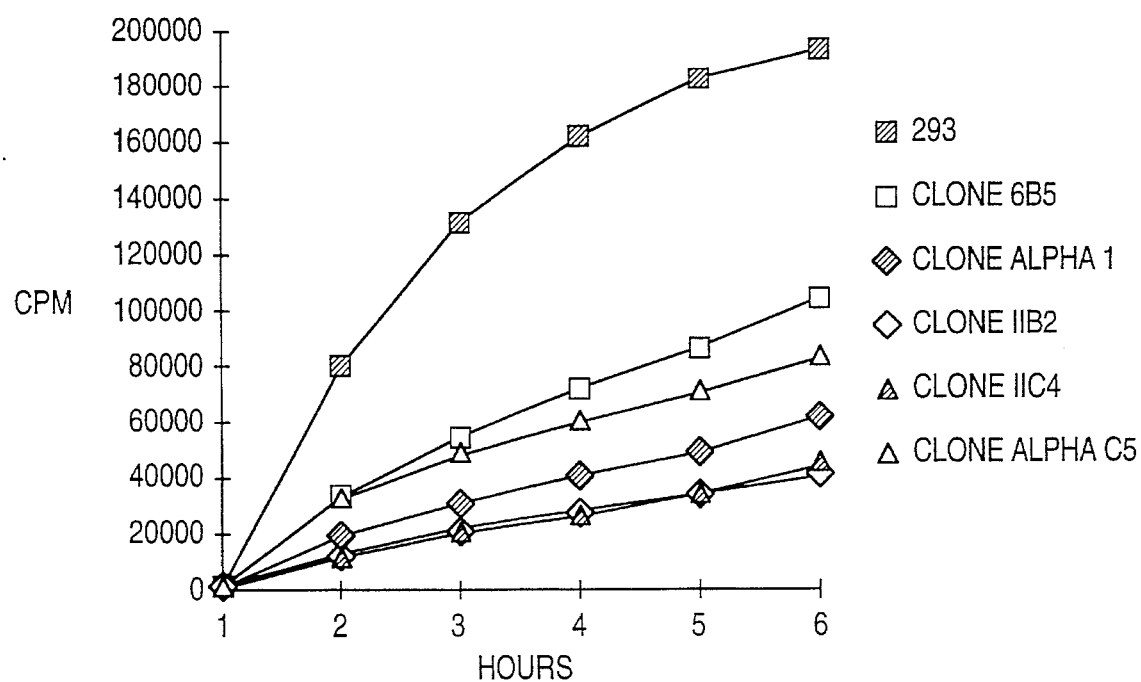

Inhibition of HIV LTR-Directed Gene Expression in Clonal Cell Lines and The Presence of HIV-Specific RNA Transcripts in Clonal Cell Lines To examine the ability of clonal cell lines expressing HIV antisense RNA to inhibit HIV LTR directed gene expression, a plasmid containing the chloramphenicol acetyltransferase gene (CAT) driven by the HIV-1 LTR (pBennCAT, Gendelman) and a plasmid that expresses the first coding exon of Tat (pAR) were cotransfected into 293 cells and several clones. In this system, CAT expression is dependent upon the expression of Tat and the subsequent interaction of Tat with TAR in the HIV LTR. A range of inhibitory activity relative to 293 cells (50 to 95% inhibition) was found among the clones tested (FIG. 3A). This differential degree of HIV inhibition may be due to a variation in the number of integrated copies of the antisense-encoding vector. However, all antisense expressing clones demonstrated a significant diminution in HIV LTR-directed CAT expession.

Figure 3B:
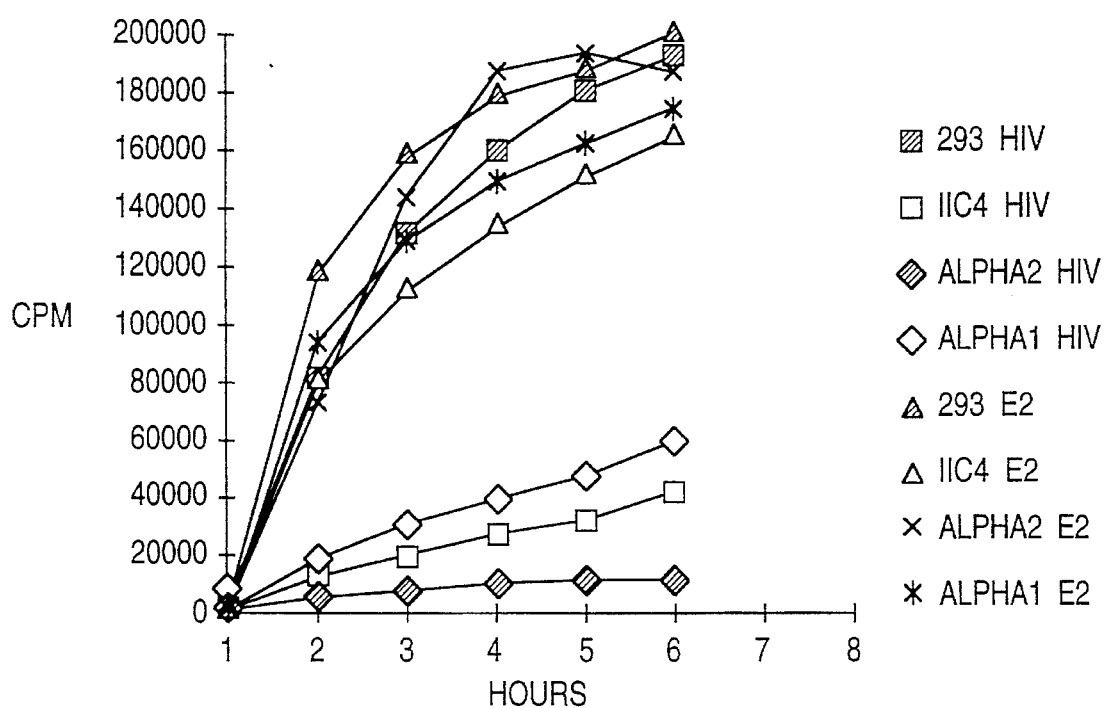
Figure 3C:
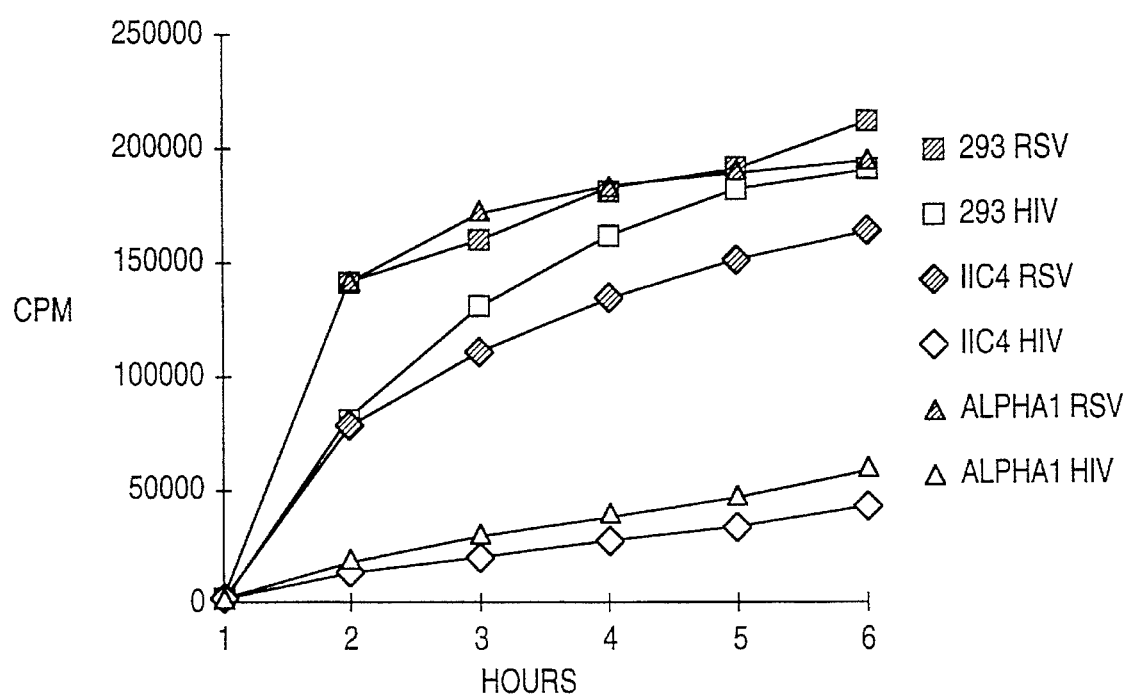

Next, the specificity of the inhibition of gene function was tested in the clones. CAT activity under the control of the adenovirus E2 promoter or the RSV LTR was compared with pBennCAT (+pAR, see above) after transfection into 293 cells or antisense expressing clones. It was predicted that only the HIV LTR-directed CAT expression should be inhibited in the clones. FIGS. 3B and 3C show that the inhibition of CAT expession is absolutely specific for the HIV LTR. The E2 promoter was clearly transactivated by the EIA protein (constitutively expressed in 293 cells, FIG. 3B), and this activity was not inhibited in the clones expressing HIV antisense RNA. Likewise, no inhibitory activity was found when CAT was expressed from a heterologous retroviral (RSV) LTR (FIG. 3C). Comparable levels of CAT activity obtained in 293 cells and antisense clones with either the E2 promoter or RSV LTR indicated that transfection efficiencies were similar in all the cell lines.

Figure 4A:
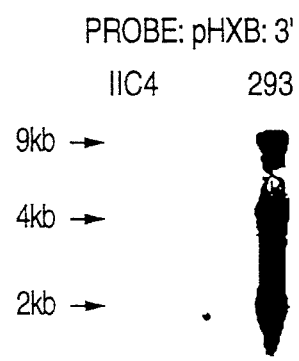
Figure 4B:
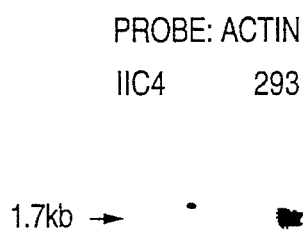
Figure 4C:
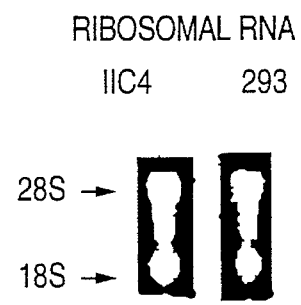

The specific inhibition of HIV LTR directed gene expression described above and the predicted mode of action of antisense RNA suggested that the accumulation of intracellular HIV RNA transcripts should be markedly reduced in antisense expressing clones. To test this hypothesis, 293 cells and one antisense clone (IIC4) were transfected with an infectious proviral DNA clone of HIV-1 (pHXB-2) and harvested total cellular RNA four days later. RNA blots were hybridized with an HIV-specific probe that contained sequences common to all HIV RNA species. As shown in FIG. 4A, all three of the major HIV RNA species (9 kb, 4 kb and 2 kb) were easily detected in 293 cell RNA. In contrast, very low levels of HIV RNA were present in the llC4 RNA blot (even after prolonged exposures of the radioautograph). Similar amounts of RNA were loaded in each lane as evidenced by equivalent amounts of actin (FIG. 4B) or ribosomal RNA (FIG. 4C). Therefore, clones expressing HIV antisense RNA clearly inhibited the accumulation of intracellular HIV RNA transcripts.

EXAMPLE 7

Inhibition of HIV Replication in Antisense Expressing Clones

The observed inhibition of HIV transcription in clones expressing antisense RNA suggested that virus production in these cells might also be impaired. Therefore, we assayed several clones for the production of virus (as judged by the presence of reverse transcriptase activity in culture supernatants) three days after transfection with pHXB-2. As shown in FIG. 5, each of the three clones tested produced significantly less virus than the control 293 cells. The level of inhibition ranged from 70 to 90%, and did not vary significantly with the amount of transfected HIV plasmid DNA. In separate experiments, inhibition of virus production was evident one day after transfection, and plateaued at maximal levels for day two through day eight (the last day tested, FIG. 6). Transfection efficiencies in all clones tested clones was controlled for by the use of E2-CAT as an indicator plasmid (see figure descriptions).

To test the specificity of inhibition of retrovirus replication, the production of HIV and SIV, two related but genetically distinct primate lentiviruses was compared, after transfection of infectious proviral DNA clones into 293 cells or antisense clones. As shown in FIG. 7, SIV production tested. The significant inhibition of SIV production was likely due to the sequence similarity in SIV TAR and HIV-1 TAR.

In one experiment, supernatant fluids from 293 and two clonal lines were removed (alpha-2 and IIC4) 24 hours after transfection with pHXB-2 and assayed for the relative amounts of infectious virus by titration on a human $CD4^+$ lymphocyte cell line (CEMX174). In concordance with the data on virus production, both cell lines inhibited the production of infectious HIV relative to the control 293 cells (alpha-2, 75% and IIC4 51% vs 293 cells).

EXAMPLE 8

Establishment of an AAV-Transduced Human $CD4^+$ Lymphocyte Cell Line Expressing HIV Antisense RNA To further demonstrate the utility of the vector system described above, infectious stocks of the HIV antisense-encoding recombinant AAV genome were used. Encapsidation was achieved by cotransfecting the AAV vector plasmid and a helper plasmid (pTAAV) that contains all the AAV endogenous promoters and coding sequences, but lacks the ITRs and encapsidation signal, into helper virus-infected cells. The results AAV stock was used to transduce a human $CD4^+$ lymphocyte cell line (H9) and the cells were subsequently propagated in bulk in G418-containing medium. Transduced and untransduced H9 cells were infected in parallel with cell-free HIV-1. When compared to the untransduced H9 cells, the antisense-transduced cells reduction in reverse transcriptase activity in culture supernatants on day six after infection. These data suggest that encapsidated AAV vectors can be used to deliver HIV-specific antisense DNA to host cells.

EXAMPLE 9

Enzyme Assays

CAT assays were performed by the fluor diffusion method (Neumann et al., *Biotechniques*, 5:444–446, (1987); Crabb et al., *Anal. Biochem.* 163:88–92 (1987) $^{14}$C-chloramphenicol released into the organic fluor following acetylation, was measured by scintillation counting at time 0 and at hourly intervals thereafter. Purified CAT (Boehringer Mannheim Biochemicals) was used to generate standard curves and served as positive control for the assays.

REFERENCES

Marks et al., *Rev. Infect. Dis.* 11:474–76 (1989).
Sacks et al., *Ann. Intern. Med.* 111:893–99 (1989).
Smith et al., *Proc. Natl. Acad. Sci. USA* 83:2787–91 (1986).
Kulka et al., *Proc. Natl. Acad. Sci. USA* 86:6868–72 (1989).
Friedman et al., *Nature* 335:395–96 (1988).
Buller et al., *J. Virol.* 40:241–47 (1981).
Lebkowski et al., *Mol. Cell. Biol.* 8:3988–96 (1988).
McGeoch et al., *Nucl. Acids Res.* 14:1727–45 (1986).
Green et al., *Ann. Rev. Biochem.* 55:596–97 (1986).
Green et al., *Cell* 58:215–23 (1989).
Herskowitz et al., *Nature* 329:219–22 (1987).
Malim et al., *Cell* 58:205–14 (1989).
Rosenberg et al., *Nature* 313:703–706 (1985).
Crowley et al., *Cell* 43:633–41 (1985).
Melton, *Proc. Natl. Acad. Sci. USA* 82:144–48 (1985).
Ratner et al., *Nature* 313:277–84 (1985).
Lusso et al., *Science* 247:848–51 (1990).
Neumann et al., *Biotechniques* 5:444–48 (1987).
Crabb et al., *Anal. Biochem.* 163:88–92 (1987).
von Ruden et al., *J. Virol.* 63:677–82 (1989).
Agrawal et al., *Proc. Natl. Acad. Sci. USA* 86:7790–94 (1989).
Matsukara et al., *Proc. Natl. Acad. Sci. USA* 84:7706–10 (1987).
Smith et al., *Proc. Natl. Acad. Sci. USA* 83:2787–91 (1986).
Hoggan et al., *Proc. Natl. Acad. Sci. USA* 55:1457–47 (1966).
Janik et al., *Proc. Natl. Acad. Sci.* 78:1925–29 (1981).
Actchison et al., *Science* 149:754–56 (1965).
Graham et al., *Virology* 34:402–09 (1980).
Lusby et al., *J. Virol.* 34:402–09 (1980).
Srivastava et al., *J. Virol.* 45:55–64 (1983).
Carter et al., *Nature New Biol.* 244:71–73 (1973).
Walder, *Genes and Devel.* 2:502–04 (1988).
Dash et al., *Proc. Natl. Acad. Sci. USA* 84:7896–7900 (1987).
Marcus-Sekura, *Anal. Biochem.* 172:289–95 (1988).
Izant et al., *Science* 229:334–52 (1978).
Izant et al., *Cell* 36:1007–15 (1984).
Kotin et al., *Virology* 170:460–67 (1989).
Kotin et al., *Proc. Natl. Acad. Sci.* 87:2211–15 (1990).
LaFace et al., *Virol.* 162:483–86 (1988).

What is claimed is:

1. An AAV-based vector that is suitable for transferring a heterologous DNA fragment into cells in vitro, comprising:
   (a) vector pWC3,
   (b) a heterologous promoter oriented so as to promote transcription towards the AAV polyadenylation signal of said pWC3 vector, and
   (c) a heterologous DNA fragment, wherein said heterologous DNA fragment is under the regulatory control of said heterologous promoter.

2. An AAV-based vector according to claim 1, wherein said heterologous DNA fragment encodes an antisense polynucleotide sequence that is complementary to a targeted RNA sequence.

3. An AAV-based vector according to claim 1, wherein said heterologous DNA fragment is a gene that encodes a protein of interest.

4. An AAV-based vector according to claim 2, further comprising:
   (d) a second heterologous promoter oriented so as to promote transcription in a direction opposite to said heterologous promoter of (b), and
   (e) a second heterologous DNA fragment, wherein said second heterologous DNA fragment is either a gene that encodes a selectable marker or is a gene that encodes an enzymatically measurable marker protein, and wherein said second heterologous DNA fragment is under the regulatory control of said second heterologous promoter.

5. An AAV-based vector according to claim 4, wherein said targeted RNA sequence is ICP4 of herpes simplex virus.

6. An AAV-based vector according to claim 4, wherein said targeted RNA sequence is E1a of adenovirus.

7. An AAV-based vector according to claim 4, wherein said targeted RNA sequence is HIV-1 TAR.

8. An AAV-based vector according to claim 7, wherein said vector is pCWRSV-HIVAlpha-Neo.

9. An AAV-based vector according to claim 1, wherein said heterologous promoter is the Rous sarcoma virus promoter.

10. An AAV-based vector which is pWC3.

11. An AAV-based vector which is pCWRSV.

* * * * *